United States Patent
Pascual et al.

(10) Patent No.: US 7,910,113 B2
(45) Date of Patent: Mar. 22, 2011

(54) TOLERIZING AGENTS

(75) Inventors: David W. Pascual, Bozeman, MT (US);
Kohtaro Fujihashi, Hoover, AL (US);
Massimo Maddaloni, Bozeman, MT (US)

(73) Assignees: Montana State University, Bozeman, MT (US); UAB Research Foundation, Birmingham, AL (US)

( * ) Notice: Subject to any disclaimer, the term of this patent is extended or adjusted under 35 U.S.C. 154(b) by 0 days.

(21) Appl. No.: 12/294,380

(22) PCT Filed: Mar. 27, 2007

(86) PCT No.: PCT/US2007/065278
§ 371 (c)(1),
(2), (4) Date: Sep. 24, 2008

(87) PCT Pub. No.: WO2007/112410
PCT Pub. Date: Oct. 4, 2007

(65) Prior Publication Data
US 2009/0169578 A1    Jul. 2, 2009

Related U.S. Application Data

(60) Provisional application No. 60/786,446, filed on Mar. 27, 2006.

(51) Int. Cl.
*A61K 39/15* (2006.01)
*A61K 39/00* (2006.01)
*C07K 14/14* (2006.01)
*C07K 14/00* (2006.01)

(52) U.S. Cl. .............. 424/215.1; 424/184.1; 424/192.1; 530/350

(58) Field of Classification Search ................. None
See application file for complete search history.

(56) References Cited

U.S. PATENT DOCUMENTS
6,072,041 A * 6/2000 Davis et al. ................ 530/391.1

FOREIGN PATENT DOCUMENTS
WO    WO 2006/052668    5/2006
WO    WO 2006/078567    7/2006

OTHER PUBLICATIONS

Allan et al. "Rat intestinal M cells contain acidic endosomal-lysosomal compartments and express class II major histocompatibility complex determinants," *Gastroenterology*, 104:698-708, 1993.
Barton et al., "Utilization of sialic acid as a coreceptor enhances reovirus attachment by multistep adhesion strengthening," *J Biol Chem*, 276:2200-2211, 2000.
Chappell et al., "Mutations in type 3 reovirus that determine binding to sialic acid are contained in the fibrous tail domain of viral attachment protein σ1," *J. Virol*, 71:1834, 1997.
Chen et al., "Peripheral deletion of antigen-reactive T cells in oral tolerance," *Nature*, 376:177-180, 1995.
Chen et al., "Regulatory T cell clones induced by oral tolerance: suppression of autoimmune encephalomyelitis," *Science*, 265:1237-1240, 1994.
Collins et al., "Mucosal tolerance to a bacterial superantigen indicates a novel pathway to prevent toxic shock," *Infect Immun*, 70:2282-2287, 2002.
Cottrez and Groux, "Specialization in tolerance: innate CD4+ CD25+ versus acquired Tr1 and Th3 regulatory T cells," *Transplantation*, 77:S12-15, 2004.
Dieckmann et al., "Human CD4+ CD25+ regulatory, contact-dependent T cells induce interleukin 10-producing, contact-independent type 1-like regulatory T cells [corrected]," *J Exp Med*, 196:247-253, 2002.
Ermak et al., "Uptake and transport of copolymer biodegradable microspheres by rabbit Peyer's patch M cells," *Cell Tissue Res*, 279:433-436, 1995.
Friedman and Weiner, "Induction of anergy or active suppression following oral tolerance is determined by antigen dosage," *Proc Natl Acad Sci* (USA), 91:6688-6692, 1994.
Frisoni et al., "Nuclear Autoantigen Translocation and Autoantibody Opsonization Lead to Increased Dendritic Cell Phagocytosis and Presentation of Nuclear Antigens: A Novel Pathogenic Pathway for Autoimmunity?," *J Immunology*, 175:2692-2701, 2005.
Fujihashi et al., "A revisit of mucosal IgA immunity and oral tolerance," *Acta Odontol Scand*, 59:301-308, 2001.
Fujihashi et al., "g/d T cell-deficient mice have impaired mucosal immunoglobulin A responses," *J Exp Med*, 183:1929-1935, 1996.
Fujihashi et al., "Peyer's patches are required for oral tolerance to proteins," *Proc Natl Acad Sci* (USA), 98:3310-3315, 2001.
Garside et al., "Oral tolerance in disease," *Gut*, 44:137-142, 1999.
Gebert et al., "M cells in Peyer's patches of the intestine," *Int Rev Cytol*, 167:91-159, 1996.
Groux et al., "A CD4+ T-cell subset inhibits antigen-specific T-cell responses and prevents colitis," *Nature*, 389:737-742, 1997.
Gutgemann et al., "Induction of rapid T cell activation and tolerance by systemic presentation of an orally administered antigen," *Immunity*, 8:667-673, 1998.
Hagiwara et al., "Protective mucosal immunity in aging is associated with functional CD4+ T cells in nasopharyngeal-associated lymphoreticular tissue," *J Immunol*, 170:1754-1762, 2003.
Hamada et al., "Identification of multiple isolated lymphoid follicles on the antimesenteric wall of the mouse small intestine," *J Immunol*, 168:57-64, 2002.
Holt, "Mucosal immunity in relation to the development of oral tolerance/sensitization," *Allergy*, 53:16-19, 1998.
Jang et al., "Intestinal villous M cells: an antigen entry site in the mucosal epithelium," *Proc Natl Acad Sci* (USA), 101:6110-6115, 2004.

(Continued)

*Primary Examiner* — Zachariah Lucas
*Assistant Examiner* — Michelle Horning
(74) *Attorney, Agent, or Firm* — Klarquist Sparkman, LLP

(57) ABSTRACT

Described herein is the development of fusion proteins useful for inducing tolerance in a subject. In particular embodiments, the tolerizing agents are useful for influence autoimmune, inflammatory, and/or allergic reactions. Example tolerizing fusion proteins contain a targeting portion (which delivers the fusion protein) and a toleragen or allergen or other antigen to which tolerance is desired in a subject. In particular examples, it is demonstrated that a pσ1 fusion protein, when administered orally, facilitates systemic and mucosal tolerance. Also described is the nasal delivery of fusion proteins, for instance for restoring immunogenicity.

15 Claims, 7 Drawing Sheets

OTHER PUBLICATIONS

Figure 1:
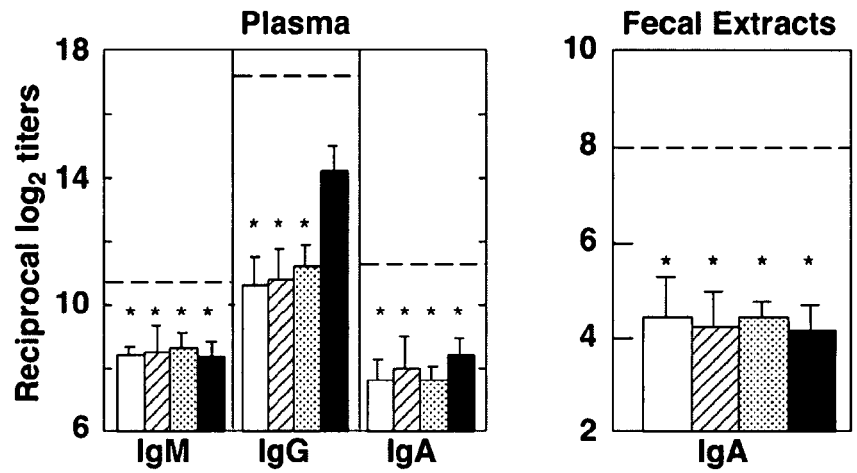

Jones et al., "*Salmonella typhimurium* initiates murine infection by penetrating and destroying the specialized epithelial M cells of the Peyer's patches," *J Exp Med*, 180:15-23, 1994.

Kataoka et al., "Nasal Flt3 ligand cDNA elicits CD11c+ CD8+ dendritic cells for enhanced mucosal immunity," *J Immunol*, 172:3612-3619, 2004.

Kato et al., "Lack of oral tolerance in aging is due to sequential loss of Peyer's patch cell interactions," *Int Immunol*, 15:145-158, 2003.

Kato et al., "Oral tolerance revisited: prior oral tolerization abrogates cholera toxin-induced mucosal IgA responses," *J Immunol*, 166:3114-3121, 2001.

Koenen et al., "A novel bispecific antihuman CD40/CD86 fusion protein with t-cell tolerizing potential," *Transplantation*, 78(10):1429-1438, 2004.

Krug et al., "TLR9-dependent recognition of MCMV by IPC and DC generates coordinated cytokine responses that activate antiviral NK cell function," *Immunity*, 21:107-119, 2004.

MacDonald, "T cell immunity to oral allergens," *Curr Opin Immunol*, 10:620-627, 1998.

Maddaloni et al., "Mucosal Vaccine Targeting Improves Onset of Mucosal and Systemic Immunity to Botulinum Neurotoxin A[1]," *J Immunology*, 177(8):5524-5532, 2006.

Mayer, "Oral tolerance: new approaches, new problems," *Clin Immunol*, 94:1-8, 2000.
Melamed and Friedman, "Direct evidence for anergy in T lymphocytes tolerized by oral administration of ovalbumin," *Eur J Immunol*, 23:935-942, 1993.
Monfardini et al., "Adoptive protection from experimental myasthenia gravis with T cells from mice treated nasally with acetylcholine receptor epitopes," *J Neuroimmunol*, 123:123-134, 2002.
Mowat, "Anatomical basis of tolerance and immunity to intestinal antigens," *Nat Rev Immunol*, 3:331-341, 2003.
Nagler-Anderson and Shi, "Peripheral nonresponsiveness to orally administered soluble protein antigens," *Crit Rev Immunol*, 21:121-131, 2001.
Nagler-Anderson et al., "Control freaks: immune regulatory cells," *Nat Immunol*, 5:119-122, 2004.
Neutra et al., "Epithelial M cells: gateways for mucosal infection and immunization," *Cell*, 86:345-348, 1996.
Ochoa-Reparaz et al., "Regulatory T cell vaccination without autoantigen protects against experimental autoimmune encephalomyelitis," *J Immunol*, 178(3):1791-1799, 2007.
Rubas et al., "Incorporation of the reovirus M cell attachment protein into small unilamellar vesicles: incorporation efficiency and binding capability to L929 cells in vitro," *J Microencapsul*, 7:385-395, 1990.
Spahn et al., "Mesenteric lymph nodes are critical for the induction of high-dose oral tolerance in the absence of Peyer's patches," *Eur J Immunol*, 32:1109-1113, 2002.
Strobel and Mowat, "Immune responses to dietary antigens: oral tolerance," *Immunol Today*, 19:173-181, 1998.
Strober et al., "Oral tolerance," *J Clin Immunol*, 18:1-30, 1998.
Sun et al., "Cholera toxin B subunit: an efficient transmucosal carrier-delivery system for induction of peripheral immunological tolerance," *Proc Natl Acad Sci* (USA), 91:10795-10799, 1994.
Tomasi, "Oral tolerance," *Transplantation*, 29:353-356, 1980.
Tsuji et al., "Antigen-specific, CD4+ CD25+ regulatory T cell clones induced in Peyer's patches," *Int Immunol*, 15:525-534, 2003.
Viney, et al., "Expanding dendritic cells in vivo enhances the induction of oral tolerance," *J Immunol*, 160:5815-5825, 1998.
Wardrop and Whitacre, "Oral tolerance in the treatment of inflammatory autoimmune diseases," *Inflamm Res*, 48:106-119, 1999.
Weiner et al., "Oral tolerance: immunologic mechanisms and treatment of animal and human organ-specific autoimmune diseases by oral administration of autoantigens," *Annu Rev Immunol*, 12:809-837, 1994.
Weiner, "Induction and mechanism of action of transforming growth factor-beta-secreting Th3 regulatory cells," *Immunol Rev*, 182:207-214, 2001.
Weiner, "Oral tolerance: immune mechanisms and the generation of Th3-type TGF—secreting regulatory cells," *Microbes & Infection*, 3:947-954, 2001.
Whitacre et al., "Oral tolerance in experimental autoimmune encephalomyelitis. III. Evidence for clonal anergy," *J Immunol*, 147:2155-2163, 1991.
Williamson et al., "Modulating dendritic cells to optimize mucosal immunization protocols," *J Immunol*, 163:3668-3675, 1999.
Winkler et al., "Mucosal tolerance as therapy of type I allergy: intranasal application of recombinant Bet v 1, the major birch pollen allergen, leads to the suppression of allergic immune responses and airway inflammation in sensitized mice," *Clin Exp Allergy*, 32:30-36, 2002.
Wolf and Bye, "The membranous epithelial (M) cell and the mucosal immune system," *Annu Rev Med*, 35:95-112, 1984.
Wu et al., "Gene transfer facilitated by a cellular targeting molecule, reovirus protein σ1," *Gene Therapy*, 7:61-69, 2000.
Wu et al., "M cell-targeted DNA vaccination," *Proc Natl Acad Sci* (USA), 98:9318-9323, 2001.

* cited by examiner

SEQUENCE LISTING

```
<160> NUMBER OF SEQ ID NOS: 12

<210> SEQ ID NO 1
<211> LENGTH: 1749
<212> TYPE: DNA
<213> ORGANISM: Adenovirus
<220> FEATURE:
<221> NAME/KEY: CDS
<222> LOCATION: (1)..(1749)

<400> SEQUENCE: 1 atg aaa cgc gcc aga ccg tct gaa gac acc ttc aac ccc gtg tat cca       48
Met Lys Arg Ala Arg Pro Ser Glu Asp Thr Phe Asn Pro Val Tyr Pro
1               5                   10                  15 tat gac aca gaa acc ggg cct cca act gtg ccc ttt ctt acc cct cca       96
Tyr Asp Thr Glu Thr Gly Pro Pro Thr Val Pro Phe Leu Thr Pro Pro
                20                  25                  30 ttt gtt tca ccc aat ggt ttc caa gaa agt ccc cct ggg gtt ctc tct      144
Phe Val Ser Pro Asn Gly Phe Gln Glu Ser Pro Pro Gly Val Leu Ser
            35                  40                  45 cta cgc gtc tcc gaa cct ttg gac acc tcc cac ggc atg ctt gcg ctt      192
Leu Arg Val Ser Glu Pro Leu Asp Thr Ser His Gly Met Leu Ala Leu
        50                  55                  60 aaa atg ggc agc ggt ctt acc cta gac aag gcc gga aac ctc acc tcc      240
Lys Met Gly Ser Gly Leu Thr Leu Asp Lys Ala Gly Asn Leu Thr Ser
65                  70                  75                  80 caa aat gta acc act gtt act cag cca ctt aaa aaa aca aag tca aac      288
Gln Asn Val Thr Thr Val Thr Gln Pro Leu Lys Lys Thr Lys Ser Asn
                85                  90                  95 ata agt ttg gac acc tcc gca cca ctt aca att acc tca ggc gcc cta      336
Ile Ser Leu Asp Thr Ser Ala Pro Leu Thr Ile Thr Ser Gly Ala Leu
                100                 105                 110 aca gtg gca acc acc gct cct ctg ata gtt act agc ggc gct ctt agc      384
Thr Val Ala Thr Thr Ala Pro Leu Ile Val Thr Ser Gly Ala Leu Ser
            115                 120                 125 gta cag tca caa gcc cca ctg acc gtg caa gac tcc aaa cta agc att      432
Val Gln Ser Gln Ala Pro Leu Thr Val Gln Asp Ser Lys Leu Ser Ile
        130                 135                 140 gct act aaa ggg ccc att aca gtg tca gat gga aag cta gcc ctg caa      480
Ala Thr Lys Gly Pro Ile Thr Val Ser Asp Gly Lys Leu Ala Leu Gln
145                 150                 155                 160 aca tca gcc ccc ctc tct ggc agt gac agc gac acc ctt act gta act      528
Thr Ser Ala Pro Leu Ser Gly Ser Asp Ser Asp Thr Leu Thr Val Thr
                165                 170                 175 gca tca ccc ccg cta act act gcc atg ggt agc ttg ggc att aac atg      576
Ala Ser Pro Pro Leu Thr Thr Ala Met Gly Ser Leu Gly Ile Asn Met
            180                 185                 190 gaa gat cct att tat gta aat aat gga aaa ata gga att aaa ata agc      624
Glu Asp Pro Ile Tyr Val Asn Asn Gly Lys Ile Gly Ile Lys Ile Ser
        195                 200                 205 ggt cct ttg caa gta gca caa aac tcc gat aca cta aca gta gtt act      672
```

```
                                           -continued
Gly Pro Leu Gln Val Ala Gln Asn Ser Asp Thr Leu Thr Val Val Thr
    210                 215                 220 gga cca ggt gtc acc gtt gaa caa aac tcc ctt aga acc aaa gtt gca         720
Gly Pro Gly Val Thr Val Glu Gln Asn Ser Leu Arg Thr Lys Val Ala
225                 230                 235                 240 gga gct att ggt tat gat tca tca aac aac atg gaa att aaa acg ggc         768
Gly Ala Ile Gly Tyr Asp Ser Ser Asn Asn Met Glu Ile Lys Thr Gly
                245                 250                 255 ggt ggc atg cgt ata aat aac aac ttg tta att cta gat gtg gat tac         816
Gly Gly Met Arg Ile Asn Asn Asn Leu Leu Ile Leu Asp Val Asp Tyr
            260                 265                 270 cca ttt gat gct caa aca aaa cta cgt ctt aaa ctg ggg cag gga ccc         864
Pro Phe Asp Ala Gln Thr Lys Leu Arg Leu Lys Leu Gly Gln Gly Pro
        275                 280                 285 ctg tat att aat gca tct cat aac ttg gac ata aac tat aac aga ggc         912
Leu Tyr Ile Asn Ala Ser His Asn Leu Asp Ile Asn Tyr Asn Arg Gly
    290                 295                 300 cta tac ctt ttt aat gca tca aac aat act aaa aaa ctg gaa gtt agc         960
Leu Tyr Leu Phe Asn Ala Ser Asn Asn Thr Lys Lys Leu Glu Val Ser
305                 310                 315                 320 ata aaa aaa tcc agt gga cta aac ttt gat aat act gcc ata gct ata        1008
Ile Lys Lys Ser Ser Gly Leu Asn Phe Asp Asn Thr Ala Ile Ala Ile
                325                 330                 335 aat gca gga aag ggt ctg gag ttt gat aca aac aca tct gag tct cca        1056
Asn Ala Gly Lys Gly Leu Glu Phe Asp Thr Asn Thr Ser Glu Ser Pro
            340                 345                 350 gat atc aac cca ata aaa act aaa att ggc tct ggc att gat tac aat        1104
Asp Ile Asn Pro Ile Lys Thr Lys Ile Gly Ser Gly Ile Asp Tyr Asn
        355                 360                 365 gaa aac ggt gcc atg att act aaa ctt gga gcg ggt tta agc ttt gac        1152
Glu Asn Gly Ala Met Ile Thr Lys Leu Gly Ala Gly Leu Ser Phe Asp
    370                 375                 380 aac tca ggg gcc att aca ata gga aac aaa aat gat gac aaa ctt acc        1200
Asn Ser Gly Ala Ile Thr Ile Gly Asn Lys Asn Asp Asp Lys Leu Thr
385                 390                 395                 400 ctg tgg aca acc cca gac cca tct cct aac tgc aga att cat tca gat        1248
Leu Trp Thr Thr Pro Asp Pro Ser Pro Asn Cys Arg Ile His Ser Asp
                405                 410                 415 aat gac tgc aaa ttt act ttg gtt ctt aca aaa tgt ggg agt caa gta        1296
Asn Asp Cys Lys Phe Thr Leu Val Leu Thr Lys Cys Gly Ser Gln Val
            420                 425                 430 cta gct act gta gct gct ttg gct gta tct gga gat ctt tca tcc atg        1344
Leu Ala Thr Val Ala Ala Leu Ala Val Ser Gly Asp Leu Ser Ser Met
        435                 440                 445 aca ggc acc gtt gca agt gtt agt ata ttc ctt aga ttt gac caa aac        1392
Thr Gly Thr Val Ala Ser Val Ser Ile Phe Leu Arg Phe Asp Gln Asn
    450                 455                 460 ggt gtt cta atg gag aac tcc tca ctt aaa aaa cat tac tgg aac ttt        1440
Gly Val Leu Met Glu Asn Ser Ser Leu Lys Lys His Tyr Trp Asn Phe
465                 470                 475                 480 aga aat ggg aac tca act aat gca aat cca tac aca aat gca gtt gga        1488
Arg Asn Gly Asn Ser Thr Asn Ala Asn Pro Tyr Thr Asn Ala Val Gly
                485                 490                 495 ttt atg cct aac ctt cta gcc tat cca aaa acc caa agt caa act gct        1536
Phe Met Pro Asn Leu Leu Ala Tyr Pro Lys Thr Gln Ser Gln Thr Ala
            500                 505                 510 aaa aat aac att gtc agt caa gtt tac ttg cat ggt gat aaa act aaa        1584
Lys Asn Asn Ile Val Ser Gln Val Tyr Leu His Gly Asp Lys Thr Lys
        515                 520                 525 cct atg ata ctt acc att aca ctt aat ggc act agt gaa tcc aca gaa        1632
```

```
Pro Met Ile Leu Thr Ile Thr Leu Asn Gly Thr Ser Glu Thr Glu
        530                 535                 540 act agc gag gta agc act tac tct atg tct ttt aca tgg tcc tgg gaa      1680
Thr Ser Glu Val Ser Thr Tyr Ser Met Ser Phe Thr Trp Ser Trp Glu
545                 550                 555                 560 agt gga aaa tac acc act gaa act ttt gct acc aac tct tac acc ttc      1728
Ser Gly Lys Tyr Thr Thr Glu Thr Phe Ala Thr Asn Ser Tyr Thr Phe
                565                 570                 575 tcc tac att gcc cag gaa taa                                          1749
Ser Tyr Ile Ala Gln Glu
            580

<210> SEQ ID NO 2
<211> LENGTH: 582
<212> TYPE: PRT
<213> ORGANISM: Adenovirus

<400> SEQUENCE: 2

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Val Ser Glu Pro Leu Asp Thr Ser His Gly Met Leu Ala Leu
    50                  55                  60

Lys Met Gly Ser Gly Leu Thr Leu Asp Lys Ala Gly Asn Leu Thr Ser
65                  70                  75                  80

Gln Asn Val Thr Thr Val Thr Gln Pro Leu Lys Lys Thr Lys Ser Asn
                85                  90                  95

Ile Ser Leu Asp Thr Ser Ala Pro Leu Thr Ile Thr Ser Gly Ala Leu
            100                 105                 110

Thr Val Ala Thr Thr Ala Pro Leu Ile Val Thr Ser Gly Ala Leu Ser
        115                 120                 125

Val Gln Ser Gln Ala Pro Leu Thr Val Gln Asp Ser Lys Leu Ser Ile
    130                 135                 140

Ala Thr Lys Gly Pro Ile Thr Val Ser Asp Gly Lys Leu Ala Leu Gln
145                 150                 155                 160

Thr Ser Ala Pro Leu Ser Gly Ser Asp Ser Asp Thr Leu Thr Val Thr
                165                 170                 175

Ala Ser Pro Pro Leu Thr Thr Ala Met Gly Ser Leu Gly Ile Asn Met
            180                 185                 190

Glu Asp Pro Ile Tyr Val Asn Asn Gly Lys Ile Gly Ile Lys Ile Ser
        195                 200                 205

Gly Pro Leu Gln Val Ala Gln Asn Ser Asp Thr Leu Thr Val Val Thr
    210                 215                 220

Gly Pro Gly Val Thr Val Glu Gln Asn Ser Leu Arg Thr Lys Val Ala
225                 230                 235                 240

Gly Ala Ile Gly Tyr Asp Ser Ser Asn Asn Met Glu Ile Lys Thr Gly
                245                 250                 255

Gly Gly Met Arg Ile Asn Asn Asn Leu Leu Ile Leu Asp Val Asp Tyr
            260                 265                 270

Pro Phe Asp Ala Gln Thr Lys Leu Arg Leu Lys Leu Gly Gln Gly Pro
        275                 280                 285

Leu Tyr Ile Asn Ala Ser His Asn Leu Asp Ile Asn Tyr Asn Arg Gly
    290                 295                 300
```

```
Leu Tyr Leu Phe Asn Ala Ser Asn Asn Thr Lys Lys Leu Glu Val Ser
305                 310                 315                 320

Ile Lys Lys Ser Ser Gly Leu Asn Phe Asp Asn Thr Ala Ile Ala Ile
                325                 330                 335

Asn Ala Gly Lys Gly Leu Glu Phe Asp Thr Asn Thr Ser Glu Ser Pro
            340                 345                 350

Asp Ile Asn Pro Ile Lys Thr Lys Ile Gly Ser Gly Ile Asp Tyr Asn
        355                 360                 365

Glu Asn Gly Ala Met Ile Thr Lys Leu Gly Ala Gly Leu Ser Phe Asp
    370                 375                 380

Asn Ser Gly Ala Ile Thr Ile Gly Asn Lys Asn Asp Asp Lys Leu Thr
385                 390                 395                 400

Leu Trp Thr Thr Pro Asp Pro Ser Pro Asn Cys Arg Ile His Ser Asp
                405                 410                 415

Asn Asp Cys Lys Phe Thr Leu Val Leu Thr Lys Cys Gly Ser Gln Val
            420                 425                 430

Leu Ala Thr Val Ala Ala Leu Ala Val Ser Gly Asp Leu Ser Ser Met
        435                 440                 445

Thr Gly Thr Val Ala Ser Val Ser Ile Phe Leu Arg Phe Asp Gln Asn
    450                 455                 460

Gly Val Leu Met Glu Asn Ser Ser Leu Lys Lys His Tyr Trp Asn Phe
465                 470                 475                 480

Arg Asn Gly Asn Ser Thr Ala Asn Pro Tyr Thr Asn Ala Val Gly
                485                 490                 495

Phe Met Pro Asn Leu Leu Ala Tyr Pro Lys Thr Gln Ser Gln Thr Ala
                500                 505                 510

Lys Asn Asn Ile Val Ser Gln Val Tyr Leu His Gly Asp Lys Thr Lys
            515                 520                 525

Pro Met Ile Leu Thr Ile Thr Leu Asn Gly Thr Ser Glu Ser Thr Glu
        530                 535                 540

Thr Ser Glu Val Ser Thr Tyr Ser Met Ser Phe Thr Trp Ser Trp Glu
545                 550                 555                 560

Ser Gly Lys Tyr Thr Thr Glu Thr Phe Ala Thr Asn Ser Tyr Thr Phe
                565                 570                 575

Ser Tyr Ile Ala Gln Glu
            580

<210> SEQ ID NO 3
<211> LENGTH: 1416
<212> TYPE: DNA
<213> ORGANISM: Reovirus
<220> FEATURE:
<221> NAME/KEY: CDS
<222> LOCATION: (13)..(1380)

<400> SEQUENCE: 3
gctattggtc gg atg gat cct cgc cta cgt gaa gaa gta gta cgg ctg ata      51
            Met Asp Pro Arg Leu Arg Glu Glu Val Val Arg Leu Ile
            1               5                   10 atc gca tta acg agt gat aat gga gca tca ctg tca aaa ggg ctt gaa       99
Ile Ala Leu Thr Ser Asp Asn Gly Ala Ser Leu Ser Lys Gly Leu Glu
15                  20                  25 tca agg gtc tcg gcg ctc gag aag acg tct caa ata cac tct gat act      147
Ser Arg Val Ser Ala Leu Glu Lys Thr Ser Gln Ile His Ser Asp Thr
    30                  35                  40                  45 atc ctc cgg atc acc cag gga ctc gat gat gca aac aaa cga atc atc      195
Ile Leu Arg Ile Thr Gln Gly Leu Asp Asp Ala Asn Lys Arg Ile Ile
            50                  55                  60
```

| | | | | | | | | | | | | | | | |
|---|---|---|---|---|---|---|---|---|---|---|---|---|---|---|---|
| gct | ctt | gag | caa | agt | cgg | gat | gac | ttg | gtt | gca | tca | gtc | agt | gat | gct | 243 |
| Ala | Leu | Glu | Gln | Ser | Arg | Asp | Asp | Leu | Val | Ala | Ser | Val | Ser | Asp | Ala | |
| | | | 65 | | | | 70 | | | | 75 | | | | | |

| caa | ctt | gca | atc | tcc | aga | ttg | gaa | agc | tct | atc | gga | gcc | ctc | caa | aca | 291 |
|---|---|---|---|---|---|---|---|---|---|---|---|---|---|---|---|---|
| Gln | Leu | Ala | Ile | Ser | Arg | Leu | Glu | Ser | Ser | Ile | Gly | Ala | Leu | Gln | Thr | |
| | | 80 | | | | | 85 | | | | | 90 | | | | |

| gtt | gtc | aat | gga | ctt | gat | tcg | agt | gtt | acc | cag | ttg | ggt | gct | cga | gtg | 339 |
|---|---|---|---|---|---|---|---|---|---|---|---|---|---|---|---|---|
| Val | Val | Asn | Gly | Leu | Asp | Ser | Ser | Val | Thr | Gln | Leu | Gly | Ala | Arg | Val | |
| | 95 | | | | | 100 | | | | | | 105 | | | | |

| gga | caa | ctt | gag | aca | gga | ctt | gca | gac | gta | cgc | gtt | gat | cac | gac | aat | 387 |
|---|---|---|---|---|---|---|---|---|---|---|---|---|---|---|---|---|
| Gly | Gln | Leu | Glu | Thr | Gly | Leu | Ala | Asp | Val | Arg | Val | Asp | His | Asp | Asn | |
| 110 | | | | | 115 | | | | | 120 | | | | | 125 | |

| ctc | gtt | gcg | aga | gtg | gat | act | gca | gaa | cgt | aac | att | gga | tca | ttg | acc | 435 |
|---|---|---|---|---|---|---|---|---|---|---|---|---|---|---|---|---|
| Leu | Val | Ala | Arg | Val | Asp | Thr | Ala | Glu | Arg | Asn | Ile | Gly | Ser | Leu | Thr | |
| | | | | 130 | | | | | 135 | | | | | 140 | | |

| act | gag | cta | tca | act | ctg | acg | tta | cga | gta | aca | tcc | ata | caa | gcg | gat | 483 |
|---|---|---|---|---|---|---|---|---|---|---|---|---|---|---|---|---|
| Thr | Glu | Leu | Ser | Thr | Leu | Thr | Leu | Arg | Val | Thr | Ser | Ile | Gln | Ala | Asp | |
| | | | | 145 | | | | | 150 | | | | | 155 | | |

| ttc | gaa | tct | agg | ata | tcc | acg | tta | gag | cgc | acg | gcg | gtc | act | agc | gcg | 531 |
|---|---|---|---|---|---|---|---|---|---|---|---|---|---|---|---|---|
| Phe | Glu | Ser | Arg | Ile | Ser | Thr | Leu | Glu | Arg | Thr | Ala | Val | Thr | Ser | Ala | |
| | | | 160 | | | | | 165 | | | | | 170 | | | |

| gga | gct | ccc | ctc | tca | atc | cgt | aat | aac | cgt | atg | acc | atg | gga | tta | aat | 579 |
|---|---|---|---|---|---|---|---|---|---|---|---|---|---|---|---|---|
| Gly | Ala | Pro | Leu | Ser | Ile | Arg | Asn | Asn | Arg | Met | Thr | Met | Gly | Leu | Asn | |
| | 175 | | | | | 180 | | | | | 185 | | | | | |

| gat | gga | ctc | acg | ttg | tca | ggg | aat | aat | ctc | gcc | atc | cga | ttg | cca | gga | 627 |
|---|---|---|---|---|---|---|---|---|---|---|---|---|---|---|---|---|
| Asp | Gly | Leu | Thr | Leu | Ser | Gly | Asn | Asn | Leu | Ala | Ile | Arg | Leu | Pro | Gly | |
| 190 | | | | | 195 | | | | | 200 | | | | | 205 | |

| aat | acg | ggt | ctg | aat | att | caa | aat | ggt | gga | ctt | cag | ttt | cga | ttt | aat | 675 |
|---|---|---|---|---|---|---|---|---|---|---|---|---|---|---|---|---|
| Asn | Thr | Gly | Leu | Asn | Ile | Gln | Asn | Gly | Gly | Leu | Gln | Phe | Arg | Phe | Asn | |
| | | | | 210 | | | | | 215 | | | | | 220 | | |

| act | gat | caa | ttc | cag | ata | gtt | aat | aat | aac | ttg | act | ctc | aag | acg | act | 723 |
|---|---|---|---|---|---|---|---|---|---|---|---|---|---|---|---|---|
| Thr | Asp | Gln | Phe | Gln | Ile | Val | Asn | Asn | Asn | Leu | Thr | Leu | Lys | Thr | Thr | |
| | | | 225 | | | | | 230 | | | | | 235 | | | |

| gtg | ttt | gat | tct | atc | aac | tca | agg | ata | ggc | gca | act | gag | caa | agt | tac | 771 |
|---|---|---|---|---|---|---|---|---|---|---|---|---|---|---|---|---|
| Val | Phe | Asp | Ser | Ile | Asn | Ser | Arg | Ile | Gly | Ala | Thr | Glu | Gln | Ser | Tyr | |
| | | 240 | | | | | 245 | | | | | 250 | | | | |

| gtg | gcg | tcg | gca | gtg | act | ccc | ttg | aga | tta | aac | agt | agc | acg | aag | gtg | 819 |
|---|---|---|---|---|---|---|---|---|---|---|---|---|---|---|---|---|
| Val | Ala | Ser | Ala | Val | Thr | Pro | Leu | Arg | Leu | Asn | Ser | Ser | Thr | Lys | Val | |
| | 255 | | | | | 260 | | | | | 265 | | | | | |

| ctg | gat | atg | cta | ata | gac | agt | tca | aca | ctt | gaa | att | aat | tct | agt | gga | 867 |
|---|---|---|---|---|---|---|---|---|---|---|---|---|---|---|---|---|
| Leu | Asp | Met | Leu | Ile | Asp | Ser | Ser | Thr | Leu | Glu | Ile | Asn | Ser | Ser | Gly | |
| 270 | | | | | 275 | | | | | 280 | | | | | 285 | |

| cag | cta | act | gtt | aga | tcg | aca | tcc | ccg | aat | ttg | agg | tat | ccg | ata | gct | 915 |
|---|---|---|---|---|---|---|---|---|---|---|---|---|---|---|---|---|
| Gln | Leu | Thr | Val | Arg | Ser | Thr | Ser | Pro | Asn | Leu | Arg | Tyr | Pro | Ile | Ala | |
| | | | | 290 | | | | | 295 | | | | | 300 | | |

| gat | gtt | agc | ggc | ggt | atc | gga | atg | agt | cca | aat | tat | agg | ttt | agg | cag | 963 |
|---|---|---|---|---|---|---|---|---|---|---|---|---|---|---|---|---|
| Asp | Val | Ser | Gly | Gly | Ile | Gly | Met | Ser | Pro | Asn | Tyr | Arg | Phe | Arg | Gln | |
| | | | 305 | | | | | 310 | | | | | 315 | | | |

| agc | atg | tgg | ata | gga | att | gtc | tcc | tat | tct | ggt | agt | ggg | ctg | aat | tgg | 1011 |
|---|---|---|---|---|---|---|---|---|---|---|---|---|---|---|---|---|
| Ser | Met | Trp | Ile | Gly | Ile | Val | Ser | Tyr | Ser | Gly | Ser | Gly | Leu | Asn | Trp | |
| | | 320 | | | | | 325 | | | | | 330 | | | | |

| agg | gta | cag | gtg | aac | tcc | gac | att | ttt | att | gta | gat | gat | tac | ata | cat | 1059 |
|---|---|---|---|---|---|---|---|---|---|---|---|---|---|---|---|---|
| Arg | Val | Gln | Val | Asn | Ser | Asp | Ile | Phe | Ile | Val | Asp | Asp | Tyr | Ile | His | |
| 335 | | | | | 340 | | | | | 345 | | | | | | |

| ata | tgt | ctt | cca | gct | ttt | gac | ggt | ttc | tct | ata | gct | gac | ggt | gga | gat | 1107 |
|---|---|---|---|---|---|---|---|---|---|---|---|---|---|---|---|---|
| Ile | Cys | Leu | Pro | Ala | Phe | Asp | Gly | Phe | Ser | Ile | Ala | Asp | Gly | Gly | Asp | |
| 350 | | | | | 355 | | | | | 360 | | | | | 365 | |

| cta | tcg | ttg | aac | ttt | gtt | acc | gga | ttg | tta | cca | ccg | tta | ctt | aca | gga | 1155 |
|---|---|---|---|---|---|---|---|---|---|---|---|---|---|---|---|---|
| Leu | Ser | Leu | Asn | Phe | Val | Thr | Gly | Leu | Leu | Pro | Pro | Leu | Leu | Thr | Gly | |
| | | | 370 | | | | | 375 | | | | | 380 | | | |

-continued

```
gac act gag ccc gct ttt cat aat gac gtg gtc aca tat gga gca cag    1203
Asp Thr Glu Pro Ala Phe His Asn Asp Val Val Thr Tyr Gly Ala Gln
            385                 390                 395 act gta gct ata ggg ttg tcg tcg ggt ggt gcg cct cag tat atg agt    1251
Thr Val Ala Ile Gly Leu Ser Ser Gly Gly Ala Pro Gln Tyr Met Ser
        400                 405                 410 aag aat ctg tgg gtg gag cag tgg cag gat gga gta ctt cgg tta cgt    1299
Lys Asn Leu Trp Val Glu Gln Trp Gln Asp Gly Val Leu Arg Leu Arg
    415                 420                 425 gtt gag ggg ggt ggc tca att acg cac tca aac agt aag tgg cct gcc    1347
Val Glu Gly Gly Gly Ser Ile Thr His Ser Asn Ser Lys Trp Pro Ala
430                 435                 440                 445 atg acc gtt tcg tac ccg cgt agt ttc acg tga ggatcagacc accccgcggc   1400
Met Thr Val Ser Tyr Pro Arg Ser Phe Thr
                450                 455 actggggcat ttcatc                                                  1416

<210> SEQ ID NO 4
<211> LENGTH: 455
<212> TYPE: PRT
<213> ORGANISM: Reovirus

<400> SEQUENCE: 4

Met Asp Pro Arg Leu Arg Glu Val Val Arg Leu Ile Ile Ala Leu
1               5                   10                  15

Thr Ser Asp Asn Gly Ala Ser Leu Ser Lys Gly Leu Glu Ser Arg Val
                20                  25                  30

Ser Ala Leu Glu Lys Thr Ser Gln Ile His Ser Asp Thr Ile Leu Arg
            35                  40                  45

Ile Thr Gln Gly Leu Asp Asp Ala Asn Lys Arg Ile Ile Ala Leu Glu
        50                  55                  60

Gln Ser Arg Asp Asp Leu Val Ala Ser Val Ser Asp Ala Gln Leu Ala
65                  70                  75                  80

Ile Ser Arg Leu Glu Ser Ser Ile Gly Ala Leu Gln Thr Val Val Asn
                85                  90                  95

Gly Leu Asp Ser Ser Val Thr Gln Leu Gly Ala Arg Val Gly Gln Leu
            100                 105                 110

Glu Thr Gly Leu Ala Asp Val Arg Val Asp His Asp Asn Leu Val Ala
        115                 120                 125

Arg Val Asp Thr Ala Glu Arg Asn Ile Gly Ser Leu Thr Thr Glu Leu
    130                 135                 140

Ser Thr Leu Thr Leu Arg Val Thr Ser Ile Gln Ala Asp Phe Glu Ser
145                 150                 155                 160

Arg Ile Ser Thr Leu Glu Arg Thr Ala Val Thr Ser Ala Gly Ala Pro
                165                 170                 175

Leu Ser Ile Arg Asn Asn Arg Met Thr Met Gly Leu Asn Asp Gly Leu
            180                 185                 190

Thr Leu Ser Gly Asn Asn Leu Ala Ile Arg Leu Pro Gly Asn Thr Gly
        195                 200                 205

Leu Asn Ile Gln Asn Gly Gly Leu Gln Phe Arg Phe Asn Thr Asp Gln
    210                 215                 220

Phe Gln Ile Val Asn Asn Asn Leu Thr Leu Lys Thr Val Phe Asp
225                 230                 235                 240

Ser Ile Asn Ser Arg Ile Gly Ala Thr Glu Gln Ser Tyr Val Ala Ser
                245                 250                 255

Ala Val Thr Pro Leu Arg Leu Asn Ser Ser Thr Lys Val Leu Asp Met
```

```
                      260                   265                   270
Leu Ile Asp Ser Ser Thr Leu Glu Ile Asn Ser Ser Gly Gln Leu Thr
            275                   280                   285

Val Arg Ser Thr Ser Pro Asn Leu Arg Tyr Pro Ile Ala Asp Val Ser
            290                   295                   300

Gly Gly Ile Gly Met Ser Pro Asn Tyr Arg Phe Arg Gln Ser Met Trp
305                   310                   315                   320

Ile Gly Ile Val Ser Tyr Ser Gly Ser Gly Leu Asn Trp Arg Val Gln
                    325                   330                   335

Val Asn Ser Asp Ile Phe Ile Val Asp Asp Tyr Ile His Ile Cys Leu
            340                   345                   350

Pro Ala Phe Asp Gly Phe Ser Ile Ala Asp Gly Gly Asp Leu Ser Leu
            355                   360                   365

Asn Phe Val Thr Gly Leu Leu Pro Pro Leu Leu Thr Gly Asp Thr Glu
            370                   375                   380

Pro Ala Phe His Asn Asp Val Val Thr Tyr Gly Ala Gln Thr Val Ala
385                   390                   395                   400

Ile Gly Leu Ser Ser Gly Gly Ala Pro Gln Tyr Met Ser Lys Asn Leu
                    405                   410                   415

Trp Val Glu Gln Trp Gln Asp Gly Val Leu Arg Leu Arg Val Glu Gly
            420                   425                   430

Gly Gly Ser Ile Thr His Ser Asn Ser Lys Trp Pro Ala Met Thr Val
            435                   440                   445

Ser Tyr Pro Arg Ser Phe Thr
            450                   455

<210> SEQ ID NO 5
<211> LENGTH: 1062
<212> TYPE: DNA
<213> ORGANISM: Adenovirus
<220> FEATURE:
<221> NAME/KEY: CDS
<222> LOCATION: (1)..(1062)

<400> SEQUENCE: 5 atg gcc aaa cga gct cgg cta agc agc tcc ttc aat ccg gtc tac ccc      48
Met Ala Lys Arg Ala Arg Leu Ser Ser Ser Phe Asn Pro Val Tyr Pro
1               5                   10                  15 tat gaa gat gaa agc agc tca caa cac ccc ttt ata aac cct ggt ttc      96
Tyr Glu Asp Glu Ser Ser Ser Gln His Pro Phe Ile Asn Pro Gly Phe
                20                  25                  30 att tcc tca aat ggt ttt gca caa agc cca gat gga gtt cta act ctt     144
Ile Ser Ser Asn Gly Phe Ala Gln Ser Pro Asp Gly Val Leu Thr Leu
            35                  40                  45 aaa tgt gtt aat cca ctc act acc gcc agc gga ccc ctc caa ctt aaa     192
Lys Cys Val Asn Pro Leu Thr Thr Ala Ser Gly Pro Leu Gln Leu Lys
        50                  55                  60 gtt gga agc agt ctt aca gta gat act atc gat ggg tct ttg gag gaa     240
Val Gly Ser Ser Leu Thr Val Asp Thr Ile Asp Gly Ser Leu Glu Glu
65                  70                  75                  80 aat ata act gcc gca gcg cca ctc act aaa act aac cac tcc ata ggt     288
Asn Ile Thr Ala Ala Ala Pro Leu Thr Lys Thr Asn His Ser Ile Gly
                85                  90                  95 tta tta ata gga tct ggc ttg caa aca aag gat gat aaa ctt tgt tta     336
Leu Leu Ile Gly Ser Gly Leu Gln Thr Lys Asp Asp Lys Leu Cys Leu
            100                 105                 110 tcg ctg gga gat ggg ttg gta aca aag gat gat aaa cta tgt tta tcg     384
Ser Leu Gly Asp Gly Leu Val Thr Lys Asp Asp Lys Leu Cys Leu Ser
        115                 120                 125
```

| | | | | | | | | | | | | | | | | |
|---|---|---|---|---|---|---|---|---|---|---|---|---|---|---|---|---|
| ctg | gga | gat | ggg | tta | ata | aca | aaa | aat | gat | gta | cta | tgt | gcc | aaa | cta | 432 |
| Leu | Gly | Asp | Gly | Leu | Ile | Thr | Lys | Asn | Asp | Val | Leu | Cys | Ala | Lys | Leu | |
| | 130 | | | | 135 | | | | | 140 | | | | | | |
| gga | cat | ggc | ctt | gtg | ttt | gac | tct | tcc | aat | gct | atc | acc | ata | gaa | aac | 480 |
| Gly | His | Gly | Leu | Val | Phe | Asp | Ser | Ser | Asn | Ala | Ile | Thr | Ile | Glu | Asn | |
| 145 | | | | | 150 | | | | | 155 | | | | | 160 | |
| aac | acc | ttg | tgg | aca | ggc | gca | aaa | cca | agc | gcc | aac | tgt | gta | att | aaa | 528 |
| Asn | Thr | Leu | Trp | Thr | Gly | Ala | Lys | Pro | Ser | Ala | Asn | Cys | Val | Ile | Lys | |
| | | | | 165 | | | | | 170 | | | | | 175 | | |
| gag | gga | gaa | gat | tcc | cca | gac | tgt | aag | ctc | act | tta | gtt | cta | gtg | aag | 576 |
| Glu | Gly | Glu | Asp | Ser | Pro | Asp | Cys | Lys | Leu | Thr | Leu | Val | Leu | Val | Lys | |
| | | | 180 | | | | | 185 | | | | | 190 | | | |
| aat | gga | gga | ctg | ata | aat | gga | tac | ata | aca | tta | atg | gga | gcc | tca | gaa | 624 |
| Asn | Gly | Gly | Leu | Ile | Asn | Gly | Tyr | Ile | Thr | Leu | Met | Gly | Ala | Ser | Glu | |
| | | 195 | | | | | 200 | | | | | 205 | | | | |
| tat | act | aac | acc | ttg | ttt | aaa | aac | aat | caa | gtt | aca | atc | gat | gta | aac | 672 |
| Tyr | Thr | Asn | Thr | Leu | Phe | Lys | Asn | Asn | Gln | Val | Thr | Ile | Asp | Val | Asn | |
| | 210 | | | | 215 | | | | | 220 | | | | | | |
| ctc | gca | ttt | gat | aat | act | ggc | caa | att | att | act | tac | cta | tca | tcc | ctt | 720 |
| Leu | Ala | Phe | Asp | Asn | Thr | Gly | Gln | Ile | Ile | Thr | Tyr | Leu | Ser | Ser | Leu | |
| 225 | | | | | 230 | | | | | 235 | | | | | 240 | |
| aaa | agt | aac | ctg | aac | ttt | aaa | gac | aac | caa | aac | atg | gct | act | gga | acc | 768 |
| Lys | Ser | Asn | Leu | Asn | Phe | Lys | Asp | Asn | Gln | Asn | Met | Ala | Thr | Gly | Thr | |
| | | | | 245 | | | | | 250 | | | | | 255 | | |
| ata | acc | agt | gcc | aaa | ggc | ttc | atg | ccc | agc | acc | acc | gcc | tat | cca | ttt | 816 |
| Ile | Thr | Ser | Ala | Lys | Gly | Phe | Met | Pro | Ser | Thr | Thr | Ala | Tyr | Pro | Phe | |
| | | | 260 | | | | | 265 | | | | | 270 | | | |
| ata | aca | tac | gcc | act | gag | acc | cta | aat | gaa | gat | tac | att | tat | gga | gag | 864 |
| Ile | Thr | Tyr | Ala | Thr | Glu | Thr | Leu | Asn | Glu | Asp | Tyr | Ile | Tyr | Gly | Glu | |
| | | 275 | | | | | 280 | | | | | 285 | | | | |
| tgt | tac | tac | aaa | tct | acc | aat | gga | act | ctc | ttt | cca | cta | aaa | gtt | act | 912 |
| Cys | Tyr | Tyr | Lys | Ser | Thr | Asn | Gly | Thr | Leu | Phe | Pro | Leu | Lys | Val | Thr | |
| | 290 | | | | 295 | | | | | 300 | | | | | | |
| gtc | aca | cta | aac | aga | cgt | atg | tta | gct | tct | gga | atg | gcc | tat | gct | atg | 960 |
| Val | Thr | Leu | Asn | Arg | Arg | Met | Leu | Ala | Ser | Gly | Met | Ala | Tyr | Ala | Met | |
| 305 | | | | | 310 | | | | | 315 | | | | | 320 | |
| aat | ttt | tca | tgg | tct | cta | aat | gca | gag | gaa | gcc | ccg | gaa | act | acc | gaa | 1008 |
| Asn | Phe | Ser | Trp | Ser | Leu | Asn | Ala | Glu | Glu | Ala | Pro | Glu | Thr | Thr | Glu | |
| | | | | 325 | | | | | 330 | | | | | 335 | | |
| gtc | act | ctc | att | acc | tcc | ccc | ttc | ttt | ttt | tct | tat | atc | aga | gaa | gat | 1056 |
| Val | Thr | Leu | Ile | Thr | Ser | Pro | Phe | Phe | Phe | Ser | Tyr | Ile | Arg | Glu | Asp | |
| | | | 340 | | | | | 345 | | | | | 350 | | | |
| gac | tga | | | | | | | | | | | | | | | 1062 |
| Asp | | | | | | | | | | | | | | | | |

```
<210> SEQ ID NO 6
<211> LENGTH: 353
<212> TYPE: PRT
<213> ORGANISM: Adenovirus

<400> SEQUENCE: 6
```

| | | | | | | | | | | | | | | |
|---|---|---|---|---|---|---|---|---|---|---|---|---|---|---|
| Met | Ala | Lys | Arg | Ala | Arg | Leu | Ser | Ser | Ser | Phe | Asn | Pro | Val | Tyr | Pro |
| 1 | | | | 5 | | | | | 10 | | | | | 15 |

| | | | | | | | | | | | | | | |
|---|---|---|---|---|---|---|---|---|---|---|---|---|---|---|
| Tyr | Glu | Asp | Glu | Ser | Ser | Ser | Gln | His | Pro | Phe | Ile | Asn | Pro | Gly | Phe |
| | | | 20 | | | | | 25 | | | | | 30 | |

| | | | | | | | | | | | | | | |
|---|---|---|---|---|---|---|---|---|---|---|---|---|---|---|
| Ile | Ser | Ser | Asn | Gly | Phe | Ala | Gln | Ser | Pro | Asp | Gly | Val | Leu | Thr | Leu |
| | | 35 | | | | | 40 | | | | | 45 | | |

| | | | | | | | | | | | | | | |
|---|---|---|---|---|---|---|---|---|---|---|---|---|---|---|
| Lys | Cys | Val | Asn | Pro | Leu | Thr | Thr | Ala | Ser | Gly | Pro | Leu | Gln | Leu | Lys |
| | 50 | | | | | 55 | | | | | 60 | | | |

```
Val Gly Ser Ser Leu Thr Val Asp Thr Ile Asp Gly Ser Leu Glu Glu
 65                  70                  75                  80

Asn Ile Thr Ala Ala Pro Leu Thr Lys Thr Asn His Ser Ile Gly
                 85                  90                  95

Leu Leu Ile Gly Ser Gly Leu Gln Thr Lys Asp Asp Lys Leu Cys Leu
            100                 105                 110

Ser Leu Gly Asp Gly Leu Val Thr Lys Asp Asp Lys Leu Cys Leu Ser
            115                 120                 125

Leu Gly Asp Gly Leu Ile Thr Lys Asn Asp Val Leu Cys Ala Lys Leu
        130                 135                 140

Gly His Gly Leu Val Phe Asp Ser Ser Asn Ala Ile Thr Ile Glu Asn
145                 150                 155                 160

Asn Thr Leu Trp Thr Gly Ala Lys Pro Ser Ala Asn Cys Val Ile Lys
                165                 170                 175

Glu Gly Glu Asp Ser Pro Asp Cys Lys Leu Thr Leu Val Leu Val Lys
            180                 185                 190

Asn Gly Gly Leu Ile Asn Gly Tyr Ile Thr Leu Met Gly Ala Ser Glu
        195                 200                 205

Tyr Thr Asn Thr Leu Phe Lys Asn Asn Gln Val Thr Ile Asp Val Asn
210                 215                 220

Leu Ala Phe Asp Asn Thr Gly Gln Ile Ile Thr Tyr Leu Ser Ser Leu
225                 230                 235                 240

Lys Ser Asn Leu Asn Phe Lys Asp Asn Gln Asn Met Ala Thr Gly Thr
                245                 250                 255

Ile Thr Ser Ala Lys Gly Phe Met Pro Ser Thr Thr Ala Tyr Pro Phe
            260                 265                 270

Ile Thr Tyr Ala Thr Glu Thr Leu Asn Glu Asp Tyr Ile Tyr Gly Glu
        275                 280                 285

Cys Tyr Tyr Lys Ser Thr Asn Gly Thr Leu Phe Pro Leu Lys Val Thr
290                 295                 300

Val Thr Leu Asn Arg Arg Met Leu Ala Ser Gly Met Ala Tyr Ala Met
305                 310                 315                 320

Asn Phe Ser Trp Ser Leu Asn Ala Glu Glu Ala Pro Glu Thr Thr Glu
                325                 330                 335

Val Thr Leu Ile Thr Ser Pro Phe Phe Phe Ser Tyr Ile Arg Glu Asp
            340                 345                 350

Asp

<210> SEQ ID NO 7
<211> LENGTH: 972
<212> TYPE: DNA
<213> ORGANISM: Adenovirus
<220> FEATURE:
<221> NAME/KEY: CDS
<222> LOCATION: (1)..(972)

<400> SEQUENCE: 7 atg acc aag aga gtc cgg ctc agt gac tcc ttc aac cct gtc tac ccc    48
Met Thr Lys Arg Val Arg Leu Ser Asp Ser Phe Asn Pro Val Tyr Pro
 1               5                  10                  15 tat gaa gat gaa agc acc tcc caa cac ccc ttt ata aac cca ggg ttt    96
Tyr Glu Asp Glu Ser Thr Ser Gln His Pro Phe Ile Asn Pro Gly Phe
             20                  25                  30 att tcc cca aat ggc ttc aca caa agc cca gac gga gtt ctt act tta   144
Ile Ser Pro Asn Gly Phe Thr Gln Ser Pro Asp Gly Val Leu Thr Leu
         35                  40                  45 aaa tgt tta acc cca cta aca acc aca ggc gga tct cta cag cta aaa   192
```

```
        Lys Cys Leu Thr Pro Leu Thr Thr Thr Gly Gly Ser Leu Gln Leu Lys
            50                  55                  60 gtg gga ggg gga ctt aca gtg gat gac act gat ggt acc tta caa gaa        240
Val Gly Gly Gly Leu Thr Val Asp Asp Thr Asp Gly Thr Leu Gln Glu
 65                  70                  75                  80 aac ata cgt gct aca gca ccc att act aaa aat aat cac tct gta gaa        288
Asn Ile Arg Ala Thr Ala Pro Ile Thr Lys Asn Asn His Ser Val Glu
                 85                  90                  95 cta tcc att gga aat gga tta gaa act caa aac aat aaa cta tgt gcc        336
Leu Ser Ile Gly Asn Gly Leu Glu Thr Gln Asn Asn Lys Leu Cys Ala
                100                 105                 110 aaa ttg gga aat ggg tta aaa ttt aac aac ggt gac att tgt ata aag        384
Lys Leu Gly Asn Gly Leu Lys Phe Asn Asn Gly Asp Ile Cys Ile Lys
            115                 120                 125 gat agt att aac acc tta tgg act gga ata aac cct cca cct aac tgt        432
Asp Ser Ile Asn Thr Leu Trp Thr Gly Ile Asn Pro Pro Pro Asn Cys
130                 135                 140 caa att gtg gaa aac act aat aca aat gat ggc aaa ctt act tta gta        480
Gln Ile Val Glu Asn Thr Asn Thr Asn Asp Gly Lys Leu Thr Leu Val
145                 150                 155                 160 tta gta aaa aat gga ggg ctt gtt aat ggc tac gtg tct cta gtt ggt        528
Leu Val Lys Asn Gly Gly Leu Val Asn Gly Tyr Val Ser Leu Val Gly
                165                 170                 175 gta tca gac act gtg aac caa atg ttc aca caa aag aca gca aac atc        576
Val Ser Asp Thr Val Asn Gln Met Phe Thr Gln Lys Thr Ala Asn Ile
                180                 185                 190 caa tta aga tta tat ttt gac tct tct gga aat cta tta act gag gaa        624
Gln Leu Arg Leu Tyr Phe Asp Ser Ser Gly Asn Leu Leu Thr Glu Glu
            195                 200                 205 tca gac tta aaa att cca ctt aaa aat aaa tct tct aca gcg acc agt        672
Ser Asp Leu Lys Ile Pro Leu Lys Asn Lys Ser Ser Thr Ala Thr Ser
210                 215                 220 gaa act gta gcc agc agc aaa gcc ttt atg cca agt act aca gct tat        720
Glu Thr Val Ala Ser Ser Lys Ala Phe Met Pro Ser Thr Thr Ala Tyr
225                 230                 235                 240 ccc ttc aac acc act act agg gat agt gaa aac tac att cat gga ata        768
Pro Phe Asn Thr Thr Thr Arg Asp Ser Glu Asn Tyr Ile His Gly Ile
                245                 250                 255 tgt tac tac atg act agt tat gat aga agt cta ttt ccc ttg aac att        816
Cys Tyr Tyr Met Thr Ser Tyr Asp Arg Ser Leu Phe Pro Leu Asn Ile
                260                 265                 270 tct ata atg cta aac agc cgt atg att tct tcc aat gtt gcc tat gcc        864
Ser Ile Met Leu Asn Ser Arg Met Ile Ser Ser Asn Val Ala Tyr Ala
            275                 280                 285 ata caa ttt gaa tgg aat cta aat gca agt gaa tct cca gaa agc aac        912
Ile Gln Phe Glu Trp Asn Leu Asn Ala Ser Glu Ser Pro Glu Ser Asn
        290                 295                 300 ata gct acg ctg acc aca tcc ccc ttt ttc ttt tct tac att aca gaa        960
Ile Ala Thr Leu Thr Thr Ser Pro Phe Phe Phe Ser Tyr Ile Thr Glu
305                 310                 315                 320 gac gac aac taa                                                         972
Asp Asp Asn <210> SEQ ID NO 8
<211> LENGTH: 323
<212> TYPE: PRT
<213> ORGANISM: Adenovirus

<400> SEQUENCE: 8

Met Thr Lys Arg Val Arg Leu Ser Asp Ser Phe Asn Pro Val Tyr Pro
 1               5                  10                  15
```

```
Tyr Glu Asp Glu Ser Thr Ser Gln His Pro Phe Ile Asn Pro Gly Phe
             20                  25                  30

Ile Ser Pro Asn Gly Phe Thr Gln Ser Pro Asp Gly Val Leu Thr Leu
         35                  40                  45

Lys Cys Leu Thr Pro Leu Thr Thr Gly Gly Ser Leu Gln Leu Lys
 50                  55                  60

Val Gly Gly Leu Thr Val Asp Asp Thr Asp Gly Thr Leu Gln Glu
 65                  70                  75                  80

Asn Ile Arg Ala Thr Ala Pro Ile Thr Lys Asn Asn His Ser Val Glu
             85                  90                  95

Leu Ser Ile Gly Asn Gly Leu Glu Thr Gln Asn Asn Lys Leu Cys Ala
             100                 105                 110

Lys Leu Gly Asn Gly Leu Lys Phe Asn Asn Gly Asp Ile Cys Ile Lys
             115                 120                 125

Asp Ser Ile Asn Thr Leu Trp Thr Gly Ile Asn Pro Pro Pro Asn Cys
 130                 135                 140

Gln Ile Val Glu Asn Thr Asn Thr Asn Asp Gly Lys Leu Thr Leu Val
145                 150                 155                 160

Leu Val Lys Asn Gly Gly Leu Val Asn Gly Tyr Val Ser Leu Val Gly
             165                 170                 175

Val Ser Asp Thr Val Asn Gln Met Phe Thr Gln Lys Thr Ala Asn Ile
             180                 185                 190

Gln Leu Arg Leu Tyr Phe Asp Ser Ser Gly Asn Leu Leu Thr Glu Glu
             195                 200                 205

Ser Asp Leu Lys Ile Pro Leu Lys Asn Lys Ser Ser Thr Ala Thr Ser
 210                 215                 220

Glu Thr Val Ala Ser Ser Lys Ala Phe Met Pro Ser Thr Thr Ala Tyr
225                 230                 235                 240

Pro Phe Asn Thr Thr Thr Arg Asp Ser Glu Asn Tyr Ile His Gly Ile
             245                 250                 255

Cys Tyr Tyr Met Thr Ser Tyr Asp Arg Ser Leu Phe Pro Leu Asn Ile
             260                 265                 270

Ser Ile Met Leu Asn Ser Arg Met Ile Ser Ser Asn Val Ala Tyr Ala
 275                 280                 285

Ile Gln Phe Glu Trp Asn Leu Asn Ala Ser Glu Ser Pro Glu Ser Asn
             290                 295                 300

Ile Ala Thr Leu Thr Thr Ser Pro Phe Phe Phe Ser Tyr Ile Thr Glu
305                 310                 315                 320

Asp Asp Asn

<210> SEQ ID NO 9
<211> LENGTH: 1098
<212> TYPE: DNA
<213> ORGANISM: Adenovirus
<220> FEATURE:
<221> NAME/KEY: CDS
<222> LOCATION: (1)..(1098)

<400> SEQUENCE: 9 atg tca aag agg ctc cgg gtg gaa gat gac ttc aac ccc gtc tac ccc     48
Met Ser Lys Arg Leu Arg Val Glu Asp Asp Phe Asn Pro Val Tyr Pro
 1               5                  10                  15 tat ggc tac gcg cgg aat cag aat atc ccc ttc ctc act ccc cct ttt     96
Tyr Gly Tyr Ala Arg Asn Gln Asn Ile Pro Phe Leu Thr Pro Pro Phe
             20                  25                  30 gtc tcc tcc gat gga tta aaa aac ttc ccc cct ggg gta ctg tca ctc    144
```

```
                Val Ser Ser Asp Gly Phe Lys Asn Phe Pro Pro Gly Val Leu Ser Leu
                         35                  40                  45 aaa ctg gct gat cca atc acc att acc aat ggg gat gta tcc ctc aag       192
Lys Leu Ala Asp Pro Ile Thr Ile Thr Asn Gly Asp Val Ser Leu Lys
 50                  55                  60 gtg gga ggt ggt ctc act ttg caa gat gga agc cta act gta aac cct       240
Val Gly Gly Gly Leu Thr Leu Gln Asp Gly Ser Leu Thr Val Asn Pro
 65                  70                  75                  80 aag gct cca ctg caa gtt aat act gat aaa aaa ctt gag ctt gca tat       288
Lys Ala Pro Leu Gln Val Asn Thr Asp Lys Lys Leu Glu Leu Ala Tyr
                 85                  90                  95 gat aat cca ttt gaa agt agt gct aat aaa ctt agt tta aaa gta gga       336
Asp Asn Pro Phe Glu Ser Ser Ala Asn Lys Leu Ser Leu Lys Val Gly
            100                 105                 110 cat gga tta aaa gta tta gat gaa aaa agt gct gcg ggg tta aaa gat       384
His Gly Leu Lys Val Leu Asp Glu Lys Ser Ala Ala Gly Leu Lys Asp
        115                 120                 125 tta att ggc aaa ctt gtg gtt tta aca gga aaa gga ata ggc act gaa       432
Leu Ile Gly Lys Leu Val Val Leu Thr Gly Lys Gly Ile Gly Thr Glu
130                 135                 140 aat tta gaa aat aca gat ggt agc agc aga gga att ggt ata aat gta       480
Asn Leu Glu Asn Thr Asp Gly Ser Ser Arg Gly Ile Gly Ile Asn Val
145                 150                 155                 160 aga gca aga gaa ggg ttg aca ttt gac aat gat gga tac ttg gta gca       528
Arg Ala Arg Glu Gly Leu Thr Phe Asp Asn Asp Gly Tyr Leu Val Ala
                165                 170                 175 tgg aac cca aag tat gac acg cgc aca ctt tgg aca aca cca gac aca       576
Trp Asn Pro Lys Tyr Asp Thr Arg Thr Leu Trp Thr Thr Pro Asp Thr
            180                 185                 190 tct cca aac tgc aca att gct caa gat aag gac tct aaa ctc act ttg       624
Ser Pro Asn Cys Thr Ile Ala Gln Asp Lys Asp Ser Lys Leu Thr Leu
        195                 200                 205 gta ctt aca aag tgt gga agt caa ata tta gct aat gtg tct ttg att       672
Val Leu Thr Lys Cys Gly Ser Gln Ile Leu Ala Asn Val Ser Leu Ile
210                 215                 220 gtg gtc gca gga aag tac cac atc ata aat aat aag aca aat cca aaa       720
Val Val Ala Gly Lys Tyr His Ile Ile Asn Asn Lys Thr Asn Pro Lys
225                 230                 235                 240 ata aaa agt ttt act att aaa ctg cta ttt aat aag aac gga gtg ctt       768
Ile Lys Ser Phe Thr Ile Lys Leu Leu Phe Asn Lys Asn Gly Val Leu
                245                 250                 255 tta gac aac tca aat ctt gga aaa gct tat tgg aac ttt aga agt gga       816
Leu Asp Asn Ser Asn Leu Gly Lys Ala Tyr Trp Asn Phe Arg Ser Gly
            260                 265                 270 aat tcc aat gtt tcg aca gct tat gaa aaa gca att ggt ttt atg cct       864
Asn Ser Asn Val Ser Thr Ala Tyr Glu Lys Ala Ile Gly Phe Met Pro
        275                 280                 285 aat ttg gta gcg tat cca aaa ccc agt aat tct aaa aaa tat gca aga       912
Asn Leu Val Ala Tyr Pro Lys Pro Ser Asn Ser Lys Lys Tyr Ala Arg
290                 295                 300 gac ata gtt tat gga act ata tat ctt ggt gga aaa cct gat cag cca       960
Asp Ile Val Tyr Gly Thr Ile Tyr Leu Gly Gly Lys Pro Asp Gln Pro
305                 310                 315                 320 gca gtc att aaa act acc ttt aac caa gaa act gga tgt gaa tac tct      1008
Ala Val Ile Lys Thr Thr Phe Asn Gln Glu Thr Gly Cys Glu Tyr Ser
                325                 330                 335 atc aca ttt aac ttt agt tgg tcc aaa acc tat gaa aat gtt gaa ttt      1056
Ile Thr Phe Asn Phe Ser Trp Ser Lys Thr Tyr Glu Asn Val Glu Phe
            340                 345                 350 gaa acc acc tct ttt acc ttc tcc tat att gcc caa gaa tga             1098
```

Glu Thr Thr Ser Phe Thr Phe Ser Tyr Ile Ala Gln Glu
        355                 360                 365

<210> SEQ ID NO 10
<211> LENGTH: 365
<212> TYPE: PRT
<213> ORGANISM: Adenovirus

<400> SEQUENCE: 10

Met Ser Lys Arg Leu Arg Val Glu Asp Asp Phe Asn Pro Val Tyr Pro
1               5                   10                  15

Tyr Gly Tyr Ala Arg Asn Gln Asn Ile Pro Phe Leu Thr Pro Pro Phe
            20                  25                  30

Val Ser Ser Asp Gly Phe Lys Asn Phe Pro Pro Gly Val Leu Ser Leu
        35                  40                  45

Lys Leu Ala Asp Pro Ile Thr Ile Thr Asn Gly Asp Val Ser Leu Lys
    50                  55                  60

Val Gly Gly Gly Leu Thr Leu Gln Asp Gly Ser Leu Thr Val Asn Pro
65                  70                  75                  80

Lys Ala Pro Leu Gln Val Asn Thr Asp Lys Lys Leu Glu Leu Ala Tyr
                85                  90                  95

Asp Asn Pro Phe Glu Ser Ser Ala Asn Lys Leu Ser Leu Lys Val Gly
            100                 105                 110

His Gly Leu Lys Val Leu Asp Glu Lys Ser Ala Ala Gly Leu Lys Asp
        115                 120                 125

Leu Ile Gly Lys Leu Val Val Leu Thr Gly Lys Gly Ile Gly Thr Glu
    130                 135                 140

Asn Leu Glu Asn Thr Asp Gly Ser Ser Arg Gly Ile Gly Ile Asn Val
145                 150                 155                 160

Arg Ala Arg Glu Gly Leu Thr Phe Asp Asn Asp Gly Tyr Leu Val Ala
                165                 170                 175

Trp Asn Pro Lys Tyr Asp Thr Arg Thr Leu Trp Thr Thr Pro Asp Thr
            180                 185                 190

Ser Pro Asn Cys Thr Ile Ala Gln Asp Lys Asp Ser Lys Leu Thr Leu
        195                 200                 205

Val Leu Thr Lys Cys Gly Ser Gln Ile Leu Ala Asn Val Ser Leu Ile
    210                 215                 220

Val Val Ala Gly Lys Tyr His Ile Ile Asn Asn Lys Thr Asn Pro Lys
225                 230                 235                 240

Ile Lys Ser Phe Thr Ile Lys Leu Leu Phe Asn Lys Asn Gly Val Leu
                245                 250                 255

Leu Asp Asn Ser Asn Leu Gly Lys Ala Tyr Trp Asn Phe Arg Ser Gly
            260                 265                 270

Asn Ser Asn Val Ser Thr Ala Tyr Glu Lys Ala Ile Gly Phe Met Pro
        275                 280                 285

Asn Leu Val Ala Tyr Pro Lys Pro Ser Asn Ser Lys Lys Tyr Ala Arg
    290                 295                 300

Asp Ile Val Tyr Gly Thr Ile Tyr Leu Gly Gly Lys Pro Asp Gln Pro
305                 310                 315                 320

Ala Val Ile Lys Thr Thr Phe Asn Gln Glu Thr Gly Cys Glu Tyr Ser
                325                 330                 335

Ile Thr Phe Asn Phe Ser Trp Ser Lys Thr Tyr Glu Asn Val Glu Phe
            340                 345                 350

Glu Thr Thr Ser Phe Thr Phe Ser Tyr Ile Ala Gln Glu
        355                 360                 365

<210> SEQ ID NO 11
<211> LENGTH: 1873
<212> TYPE: DNA
<213> ORGANISM: Gallus gallus
<220> FEATURE:
<221> NAME/KEY: CDS
<222> LOCATION: (66)..(1226)

<400> SEQUENCE: 11

```
gacatacagc tagaaagctg tattgccttt agcactcaag ctcaaaagac aactcagagt        60 tcacc atg ggc tcc atc ggc gca gca agc atg gaa ttt tgt ttt gat gta       110
      Met Gly Ser Ile Gly Ala Ala Ser Met Glu Phe Cys Phe Asp Val
      1               5                   10                  15 ttc aag gag ctc aaa gtc cac cat gcc aat gag aac atc ttc tac tgc         158
Phe Lys Glu Leu Lys Val His His Ala Asn Glu Asn Ile Phe Tyr Cys
                20                  25                  30 ccc att gcc atc atg tca gct cta gcc atg gta tac ctg ggt gca aaa         206
Pro Ile Ala Ile Met Ser Ala Leu Ala Met Val Tyr Leu Gly Ala Lys
        35                  40                  45 gac agc acc agg aca cag ata aat aag gtt gtt cgc ttt gat aaa ctt         254
Asp Ser Thr Arg Thr Gln Ile Asn Lys Val Val Arg Phe Asp Lys Leu
    50                  55                  60 cca gga ttc gga gac agt att gaa gct cag tgt ggc aca tct gta aac         302
Pro Gly Phe Gly Asp Ser Ile Glu Ala Gln Cys Gly Thr Ser Val Asn
65                  70                  75 gtt cac tct tca ctt aga gac atc ctc aac caa atc acc aaa cca aat         350
Val His Ser Ser Leu Arg Asp Ile Leu Asn Gln Ile Thr Lys Pro Asn
80                  85                  90                  95 gat gtt tat tcg ttc agc ctt gcc agt aga ctt tat gct gaa gag aga         398
Asp Val Tyr Ser Phe Ser Leu Ala Ser Arg Leu Tyr Ala Glu Glu Arg
                100                 105                 110 tac cca atc ctg cca gaa tac ttg cag tgt gtg aag gaa ctg tat aga         446
Tyr Pro Ile Leu Pro Glu Tyr Leu Gln Cys Val Lys Glu Leu Tyr Arg
            115                 120                 125 gga ggc ttg gaa cct atc aac ttt caa aca gct gca gat caa gcc aga         494
Gly Gly Leu Glu Pro Ile Asn Phe Gln Thr Ala Ala Asp Gln Ala Arg
        130                 135                 140 gag ctc atc aat tcc tgg gta gaa agt cag aca aat gga att atc aga         542
Glu Leu Ile Asn Ser Trp Val Glu Ser Gln Thr Asn Gly Ile Ile Arg
    145                 150                 155 aat gtc ctt cag cca agc tcc gtg gat tct caa act gca atg gtt ctg         590
Asn Val Leu Gln Pro Ser Ser Val Asp Ser Gln Thr Ala Met Val Leu
160                 165                 170                 175 gtt aat gcc att gtc ttc aaa gga ctg tgg gag aaa aca ttt aag gat         638
Val Asn Ala Ile Val Phe Lys Gly Leu Trp Glu Lys Thr Phe Lys Asp
                180                 185                 190 gaa gac aca caa gca atg cct ttc aga gtg act gag caa gaa agc aaa         686
Glu Asp Thr Gln Ala Met Pro Phe Arg Val Thr Glu Gln Glu Ser Lys
            195                 200                 205 cct gtg cag atg atg tac cag att ggt tta ttt aga gtg gca tca atg         734
Pro Val Gln Met Met Tyr Gln Ile Gly Leu Phe Arg Val Ala Ser Met
        210                 215                 220 gct tct gag aaa atg aag atc ctg gag ctt cca ttt gcc agt ggg aca         782
Ala Ser Glu Lys Met Lys Ile Leu Glu Leu Pro Phe Ala Ser Gly Thr
    225                 230                 235 atg agc atg ttg gtg ctg ttg cct gat gaa gtc tca ggc ctt gag cag         830
Met Ser Met Leu Val Leu Leu Pro Asp Glu Val Ser Gly Leu Glu Gln
240                 245                 250                 255 ctt gag agt ata atc aac ttt gaa aaa ctg act gaa tgg acc agt tct         878
Leu Glu Ser Ile Ile Asn Phe Glu Lys Leu Thr Glu Trp Thr Ser Ser
                260                 265                 270
```

```
aat gtt atg gaa gag agg aag atc aaa gtg tac tta cct cgc atg aag    926
Asn Val Met Glu Glu Arg Lys Ile Lys Val Tyr Leu Pro Arg Met Lys
            275                 280                 285 atg gag gaa aaa tac aac ctc aca tct gtc tta atg gct atg ggc att    974
Met Glu Glu Lys Tyr Asn Leu Thr Ser Val Leu Met Ala Met Gly Ile
        290                 295                 300 act gac gtg ttt agc tct tca gcc aat ctg tct ggc atc tcc tca gca    1022
Thr Asp Val Phe Ser Ser Ser Ala Asn Leu Ser Gly Ile Ser Ser Ala
    305                 310                 315 gag agc ctg aag ata tct caa gct gtc cat gca gca cat gca gaa atc    1070
Glu Ser Leu Lys Ile Ser Gln Ala Val His Ala Ala His Ala Glu Ile
320                 325                 330                 335 aat gaa gca ggc aga gag gtg gta ggg tca gag gct gga gtg gat        1118
Asn Glu Ala Gly Arg Glu Val Val Gly Ser Ala Glu Ala Gly Val Asp
                340                 345                 350 gct gca agc gtc tct gaa gaa ttt agg gct gac cat cca ttc ctc ttc    1166
Ala Ala Ser Val Ser Glu Glu Phe Arg Ala Asp His Pro Phe Leu Phe
                355                 360                 365 tgt atc aag cac atc gca acc aac gcc gtt ctc ttc ttt ggc aga tgt    1214
Cys Ile Lys His Ile Ala Thr Asn Ala Val Leu Phe Phe Gly Arg Cys
        370                 375                 380 gtt tcc cct taa aagaagaaa gctgaaaaac tctgtccctt ccaacaagac         1266
Val Ser Pro
        385 ccagagcact gtagtatcag gggtaaaatg aaaagtatgt tctctgctgc atccagactt   1326 cataaaagct ggagcttaat ctagaaaaaa aatcagaaag aaattacact gtgagaacag   1386 gtgcaattca ctttttcctt acacagagta aatactggtaa ctcatggatg aaggcttaag  1446 ggaatgaaat tggactcaca gtactgagtc atcacactga aaaatgcaac ctgatacatc   1506 agcagaaggt ttatggggga aaaatgcagc cttccaatta agccagatat ctgtatgacc   1566 aagctgctcc agaattagtc actcaaaatc tctcagatta aattatcaac tgtcaccaac   1626 cattcctatg ctgacaaggc aattgcttgt tctctgtgtt cctgatacta caaggctctt   1686 cctgacttcc taaagatgca ttataaaaat cttataattc acatttctcc ctaaactttg   1746 actcaatcat ggtatgttgg caaatatggt atattactat tcaaattgtt ttccttgtac   1806 ccatatgtaa tgggtcttgt gaatgtgctc ttttgttcct ttaatcataa taaaaacatg   1866 tttaagc                                                             1873

<210> SEQ ID NO 12
<211> LENGTH: 386
<212> TYPE: PRT
<213> ORGANISM: Gallus gallus

<400> SEQUENCE: 12

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95
```

-continued

```
Val Tyr Ser Phe Ser Leu Ala Ser Arg Leu Tyr Ala Glu Glu Arg Tyr
                100                 105                 110

Pro Ile Leu Pro Glu Tyr Leu Gln Cys Val Lys Glu Leu Tyr Arg Gly
            115                 120                 125

Gly Leu Glu Pro Ile Asn Phe Gln Thr Ala Ala Asp Gln Ala Arg Glu
            130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Thr Phe Lys Asp Glu
                180                 185                 190

Asp Thr Gln Ala Met Pro Phe Arg Val Thr Glu Gln Glu Ser Lys Pro
                195                 200                 205

Val Gln Met Met Tyr Gln Ile Gly Leu Phe Arg Val Ala Ser Met Ala
                210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
                260                 265                 270

Val Met Glu Glu Arg Lys Ile Lys Val Tyr Leu Pro Arg Met Lys Met
                275                 280                 285

Glu Glu Lys Tyr Asn Leu Thr Ser Val Leu Met Ala Met Gly Ile Thr
                290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
                340                 345                 350

Ala Ser Val Ser Glu Glu Phe Arg Ala Asp His Pro Phe Leu Phe Cys
                355                 360                 365

Ile Lys His Ile Ala Thr Asn Ala Val Leu Phe Phe Gly Arg Cys Val
                370                 375                 380

Ser Pro
385
```

TOLERIZING AGENTS

CROSS REFERENCE TO RELATED CASE(S)

This is the U.S. National Stage of International Application No. PCT/US2007/065278, filed Mar. 27, 2007, which was published in English under PCT Article 21(2), which in turn claims the benefit of U.S. provisional application No. 60/786,446, filed Mar. 27, 2006. Both applications are hereby incorporated by reference in their entirety.

STATEMENT REGARDING FEDERALLY SPONSORED RESEARCH OR DEVELOPMENT

This invention was made with government support under contracts AI018958, DE012242, AI043197, DC004976, and DE013812 awarded by the National Institutes of Health. The government has certain rights in the invention.

FIELD OF THE DISCLOSURE

This disclosure relates to agents and compositions useful in stimulating tolerance to an immunogen. In particular, it relates to mucosal targeted fusion proteins that can be applied, for instance, through oral and/or nasal routes to tolerize a subject.

BACKGROUND OF THE DISCLOSURE

Oral administration of a single high dose or repeated low doses of protein has been shown to induce systemic unresponsiveness, presumably in the presence of mucosal IgA antibody responses (Challacombe et al., *J. Exp. Med.* 152:1459-1472, 1980; Mestecky et al., "The mucosal immune system." *In Fundamental Immunology*. Paul, ed. Lippincott Williams & Wilkins, Philadelphia, Pa., 965-1020, 2003). In earlier studies, this type of immune response was dubbed oral tolerance and the concept was used to refer specifically to immune responses elicited in mucosa-associated as opposed to systemic lymphoid tissues (Tomasi, *Transplantation* 29:353-356, 1980). However, previous studies showed that tolerance induction occurred in the mucosal effector lymphoid tissues (Kato et al., *J. Immunol.* 166:3114-3121, 2001). Thus, mice fed large amounts of ovalbumin (OVA) prior to oral challenge with OVA plus native cholera toxin (CT) as mucosal adjuvant exhibited antigen (Ag)-specific unresponsiveness in both systemic and mucosal compartments, while those fed PBS showed high levels of secretory (S)-IgA Ab responses (Kato et al., *J. Immunol.* 166:3114-3121, 2001).

This unique response is an important natural physiological mechanism whereby the host presumably avoids development of hypersensitivity reactions to many ingested food proteins and other antigens (Garside et al, *Gut* 44:137-142, 1999). Thus, tolerance (or systemic unresponsiveness) represents the most common response of the host to the environment. In addition to showing tolerance to several thousand different food proteins, the host tolerates indigenous microflora which colonize the large intestine. Further, the development of mucosal tolerance against pollen and dust antigens could also be essential for the inhibition of allergic reactions, including IgE-mediated hypersensitivity. Indeed, tolerance is so strong that oral immunization only succeeds in inducing mucosal and systemic immunity when potent mucosal adjuvants, vectors or other special delivery systems are employed (Fujihashi et al, *Acta. Odontol Scand.* 59:301-308, 2001).

It is now generally agreed that oral tolerance is established and maintained at the level of T cells (Holt, *Allergy* 53:16-19, 1998; MacDonald, *Curr. Opin. Immunol.* 10:620-627, 1998; Mayer, *Clin. Immunol.* 94:1-8, 2000; Strobel & Mowat, *Immunol Today* 19:173-181, 1998; Strober et al., *J. Clin. Immunol.* 18:1-30, 1998; Wardrop & Whitacre, *Inflamm. Res.* 48:106-119, 1999; Weiner et al., *Annu. Rev. Immunol.* 12:809-837, 1994). Recent studies have identified dendritic cells as key players in the direct or indirect (via T cells) induction of oral tolerance (Mowat, *Nat. Rev. Immunol.* 3:331-341, 2003; Kato et al., *Int. Immunol.* 15:145-158, 2003; Nagler-Anderson & Shi, *Crit. Rev. Immunol.* 21:121-131. 2001; Viney et al., *J. Immunol.* 160:5815-5825, 1998; Williamson, *J. Immunol.* 163:3668-3675, 1999; Weiner, *Immunol Rev.* 182:207-214, 2001). Though the precise mechanisms by which oral delivery of Ag elicits a state of systemic unresponsiveness are not fully understood, the dosage of Ag has been shown to be an important factor (Friedman & Weiner, *Proc. Natl. Acad. Sci.* (*USA*) 91:6688-6692, 1994). For example, a high oral Ag dose leads to T cell clonal deletion or anergy, which is characterized by inhibition of both Ab- and cell-mediated immune (CMI) responses (Melamed & Friedman, *Eur. J. Immunol.* 25 23:935-942, 1993; Whitacre et al., *J. Immunol* 147:2155-2163, 1991; Chen et al., *Nature* 376:177-180, 1995). On the other hand, repeated delivery of low doses of protein induces cytokine-mediated active immune suppression characterized by the presence of regulatory T cells, which include TGF-β-producing Th3 cells and IL-10-producing T regulatory one (Tr1) cells or $CD4^+$ $CD25^+$ T regulatory (Treg) cells (Chen et al., *Science* 265:1237-1240, 1994; Groux et al., *Nature* 389:737-742, 1997; Nagler-Anderson et al., *Nat. Immunol.* 5:119-122, 2004). Regulatory-type T cells were first rediscovered as acquired-type Tr1 cells playing a central role in suppressing inflammatory bowel disease development (Groux et al., *Nature* 389:737-742, 1997). Acquired-type Treg cells, which differentiate from naïve T cells, regulate tolerance to food Ags, bacterial flora and pathogens by producing suppressive cytokines such as TGF-β1 and IL-10 (Cottrez & Groux, *Transplantation* 77:S12-15, 2004). In contrast, naturally occurring $CD4^+$ $CD25^+$ T cells or innate-type Treg cells, which are also suppressive, control the proliferation, expansion and differentiation of naïve T cells in a direct cell contact manner (Dieckmann et al., *J. Exp. Med.* 196:247-253, 2002) and migrate preferentially to lymphoid tissues, mainly the spleen (Cottrez & Groux, *Transplantation* 77:S12-15, 2004).

In addition to $CD4^+$ T cell function, gut-associated lymphoreticular tissues (GALT) play critical roles in the induction of oral tolerance. In this regard, our previous studies showed that Peyer's patch (PP)-deficient (PP-null) mice generated by in utero treatment of mothers with lymphotoxin beta-receptor (LTβR)-immunoglobulin (Ig) fusion protein failed to exhibit systemic unresponsiveness to oral protein antigens (Ag) such as OVA (Fujihashi et al., *Proc. Natl. Acad. Sci.* (*USA*) 98:3310-3315, 2001). In contrast, others reported that PPs were not required for the induction of systemic tolerance (Spahn et al., *Eur. J. Immunol* 32:1109-1113, 2002). Recent studies have shown the importance of Ag-specific $CD4^+$ $CD25^+$ Treg cell clones from PPs in oral tolerance induction. Thus, Treg cells from PP of mice given a high dose of β-lactoglobulin produced high levels of TGF-β1, and adoptive transfer of these clones reduced Ag-specific plasma IgG Ab responses (Tsuji et al., *Int. Immunol.* 15:525-534, 2003). Despite these compelling studies, the precise cellular and molecular mechanisms and the role of PPs in the induction of systemic and mucosal unresponsiveness still remain to be elucidated.

Adenoviruses enter the host via attachment to the mucosal epithelia by its protein known as "fiber protein". Likewise, reoviruses infect the host by attaching to M cells via a protein called "protein Gσ1" (pσ1; Wu et al., *Proc. Natl. Acad. Sci. (USA)* 98:9318-9323, 2001; Rubas et al., *J. Microencapsul* 7:385-395, 1990). These attachment proteins of adenovirus ssp. and reovirus ssp. are well known, and share a strikingly structural similarity despite lack of homology at the primary structure level. Both proteins are composed of a N-terminal shaft followed by a C-terminal globular domain, sometimes referred to as "head" or "knob". The shaft inserts into the viral capsids, while the globular domains contain the cell-specific targeting regions. For both of these viruses, the shaft contains a domain that causes the protein to form homotrimers, the active form of the protein.

Incorporation of pσ1 into liposomes allows the latter to bind to mouse L cells and rat Peyer's patches (Rubas et al., *J. Microencapsul* 7:385-395, 1990), and the recombinant pσ1 is also known to bind to NALT M cells (Wu et al., *Gene Ther.* 7:61-69, 2000; Wu et al., *Proc. Natl. Acad. Sci. (USA)* 98:9318-9323, 2001). In marked contrast to results seen when DNA is given alone, immunization with DNA complexed to poly-L-lysine-conjugated pσ1 leads to elevated S-IgA and plasma IgG Ab responses (Wu et al., *Proc. Natl. Acad. Sci. (USA)* 98:9318-9323, 2001).

There exists a need to develop agents that can stimulate or cause tolerance in a subject to an immunogen. It is to such agents, and compositions comprising such, that this disclosure is drawn.

Overview of Representative Embodiments

Described herein is the development of M cell-targeting Ag delivery systems using recombinant reovirus pσ1. Recombinant pσ1 of reovirus has been genetically fused to OVA (OVA-pσ1). It is demonstrated that this fusion protein, when administered orally, facilitates systemic and mucosal tolerance induction by innate- and/or acquired-types of Treg cells. Also described is the nasal delivery of a OVA-pσ1(m) or OVA-pσ1(Δ) fusion protein for restoring OVA immunogenicity.

Thus, there is provided herein a new approach to delivering highly virulent and antigen-specific tolerizing agents, which uses a ligand (such as a mucosal targeting ligand) fused to a specific antigen to induce host unresponsiveness solely to that antigen. The ligand portion of the protein can be fused a broad range of antigens (toleragens), enabling the generation of tolerance to a number of autoimmune disease antigens, inflammatory disease antigens, allergens, and biological therapeutic molecules (e.g., botulinum toxin), for instance. The fusion proteins are capable of regulating peripheral tolerance subsequent to nasal or oral application.

The tolerizing fusion proteins provided herein can be used in various tolerance applications, including but not limited to treatment or amelioration of autoimmune diseases, inflammatory diseases, allergic reactions, graft or transplant rejection, and so forth. In addition, the provided proteins and methods of their use permit continuous or on-going treatment of a subject with a biological therapeutic agent. For example, tolerance has been demonstrated in mice challenged with ovalbumin or myelin proteins, the latter being useful for treatment against multiple sclerosis.

The foregoing and other features and advantages will become more apparent from the following detailed description of several embodiments, which proceeds with reference to the accompanying figures.

DESCRIPTION OF THE DRAWINGS

FIG. 1. Optimization of OVA-pσ1 for the induction of mucosal tolerance (A). BALB/c mice were fed a single dose of OVA-pσ1 [1000 (□), 500 (▨) or 100 (▩) μg] prior to oral challenge with OVA (1 mg) plus CT as adjuvant (10 μg) three times at weekly intervals. In some experiments, mice were given three separate doses of 100 μg of OVA-pσ1 (■) at daily intervals before oral challenge. Plasma and fecal extract samples were collected seven days after the last oral challenge and subjected to OVA-specific ELISA. As a control group, mice were fed PBS prior to oral challenge with OVA plus CT (dotted line).

The results represent the mean values ±SEM for 12 mice in each experimental group and were taken from three separate experiments.

FIG. 2. Numbers of OVA-specific AFCs in various lymphoid tissues. BALB/c mice were fed three separate doses of OVA-σ1 (100 μg) at weekly intervals prior to oral challenge with OVA (1 mg) plus CT (10 μg). As controls, mice were fed PBS prior to oral challenge with OVA plus CT. Mononuclear cells from spleen, MLNs and iLP were isolated seven days after the last oral challenge and subjected to OVA-specific ELISPOT assays in order to detect anti-OVA IgM (□), IgG (▨) and IgA (■) AFCs. The results represent the mean i one standard error of the mean (SEM) for 12 mice in each experimental group and are taken from three separate experiments.

FIG. 3. OVA-specific DTH responses and OVA-specific $CD4^+$ T cell proliferative responses. (A) Six days after the last oral challenge, both OVA-pσ1 (□)- and PBS (■)-fed groups of mice were injected with 10 μg of OVA in 20 μl of PBS into the right ear pinna. PBS (20 μl) was administered to the left ear pinna as a control. The thickness of the ear was measured 24 hours later with an upright dial thickness gauge. The DTH response was expressed as the increase in ear swelling after challenge with Ag after subtraction of swelling in the control site. (B) Seven days after the last oral challenge, $CD4^+$ T cells were purified from both OVA-σ1 (□)- and PBS (■)-fed mice. Purified $CD4^+$ T cell fractions were cultured with or without one mg/ml of OVA in the presence of APCs. An aliquot of 0.5 μCi of tritiated [$^3$H]-thymidine was added during the final 18 hours of incubation, and the amount of [$^3$H]-thymidine incorporation was determined by scintillation counting. The stimulation index was determined as cpm of wells with Ag/cpm of wells without Ag (controls). The levels of [$^3$H] TdR incorporated in each control well ranged from 500 to 1,000 cpm. The results represent the mean values ±1 SEM from three separate experiments (triplicate wells/experiment).

FIG. 4. Detection of frequency of OVA-specific $CD4^+$ T cells. Mononuclear cells from the spleen, MLNs, PPs and iLPs of mice fed OVA-pσ1 or PBS were stained with FITC-conjugated anti-CD4 mAb and PE-labeled OVA/I-$A^d$ tetramer. Samples were subjected to flow cytometric analysis using FACSCalibur™. The results represent typical results and are taken from one of three separate experiments.

FIG. 5. TGF-β1 and IL-10 production by $CD4^+$ $CD25^+$ T cells. Mice were fed 100 μg of OVA-pσ1 (□) or PBS (■) before being orally immunized weekly for three weeks with 1 mg of OVA plus 10 μg of CT. (A) $CD4^+$ $CD25^+$ T cells were purified from PPs, MLNs and spleen by flow cytometry and cultured with 1 mg/ml of OVA in the presence of irradiated APCs. The levels of TGF-β1 in the culture supernatants were determined by a TGF-β1-specific ELISA. (B) Interleukin-10 production by $CD4^+CD25^+$T cell subsets in MLNs and spleen were determined by intercellular analysis. Mononuclear cells were incubated with ionomycin (1 μg/ml, SIGMA, St. Louis, Mo.) and phorbol 12-myristate 13-acetate (PMA, 25 ng/ml, SIGMA) for 6 hours and then stained with PE-labeled anti-CD4, biotinylated anti-CD25 mAbs followed by Cy5.5-streptavidin. These samples were further stained intracellularly with ALEXA FLUOR® 488-labeled anti-IL-10 mAb (JES5-16E3). The results represent the mean values ±1 SEM from three separate experiments.

Figure 6:
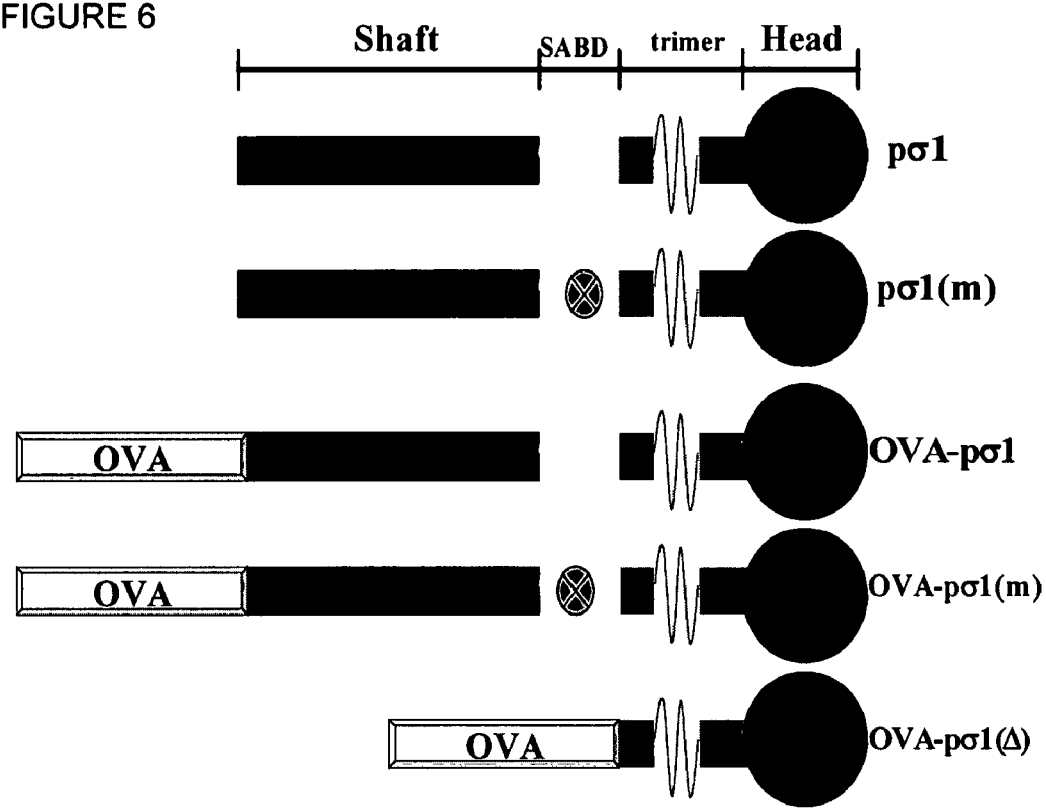

FIG. 6. Protein pσ1 (pσ1) variants described here: recombinant pσ1; pσ1(m) has a mutagenized sialic acid binding domain (SABD); OVA-pσ1; OVA-pσ1 (m) has a mutagenized SABD; and OVA-pσ1 (Δ) lacks its shaft and SABD.

Figure 7:
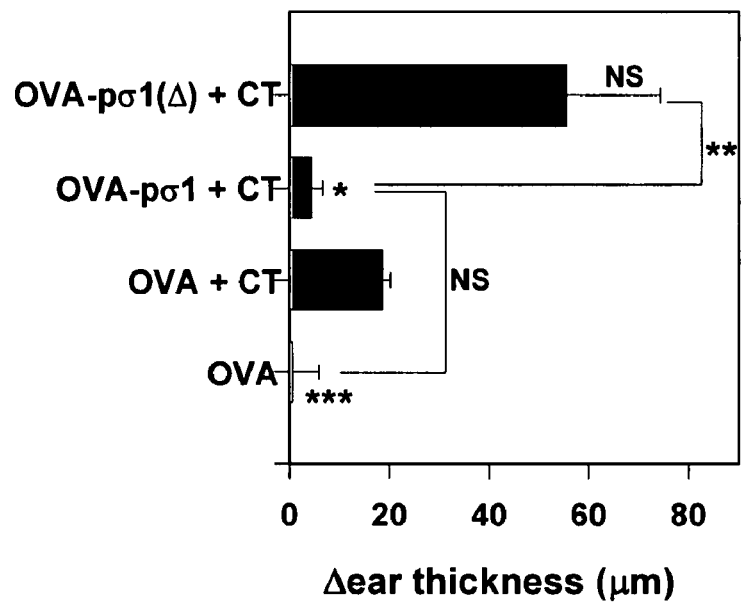

FIG. 7. OVA-pσ1 fails to elicit delayed-type hypersensitivity (DTH) responses to OVA. Mice were given three i.n. doses of OVA-pσ1+CT, OVA-pσ1(Δ)+CT, OVA+CT, or OVA alone on days 0, 7, and 14. On day 42, mice were challenged with 10 μg of OVA into one ear pinna and with sterile PBS in the other, and differences in ear swelling were measured 24 hours later. Compared to mice dosed with OVA+CT: *P<0.001, *P=0.012, and NS=not significant. Mice i.n. dosed with OVA only was not significantly different from mice i.n. dosed with OVA-pσ1+CT; mice i.n. dosed with OVA-pσ1(Δ)+CT were significantly different from OVA-pσ1+CT-dosed mice (P=0.002). Depicted were the means ±SEM of individual mice from two experiments.

Figure 8:
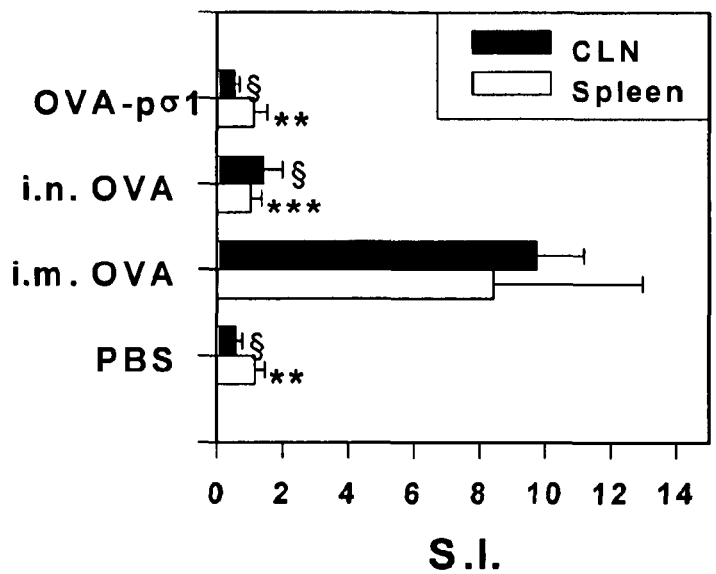

FIG. 8. CD4$^+$ T cells from mice nasally dosed with OVA-pσ1 mediate OVA unresponsiveness following adoptive transfer and peripheral OVA challenge. DO11.10 TCR CD4$^+$ T cells were adoptively transferred into naive BALB/c mice, and subsequently dosed i.n. with PBS, 400 μg OVA, or 80 μg OVA-pσ1 or i.m. with 400 μg OVA. Three days later, CLN CD4$^+$ T cells were adoptively transferred into naive BALB/c mice, and 24 hours later, they were challenged with 100 μg in incomplete Freund's adjuvant. CD4$^+$ T cells were isolated from the CLN and spleen five days later, and then cultured with mitomycin C-treated feeder (T cell-depleted) cells without or with 1.0 mg OVA for five days. $^3$H-thymidine incorporation was measured and expressed as a stimulation index (SI). For CLN, $^§P \leq 0.001$ vs. i.m. OVA; for spleen, P=0.003, *P=0.006 vs. i.m. OVA.

Figure 3:
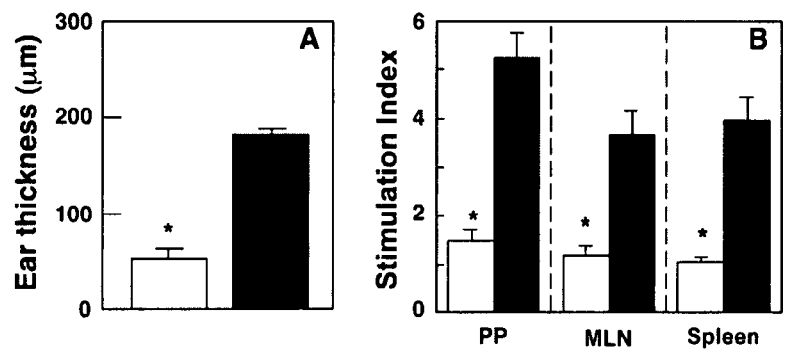
Figure 9:
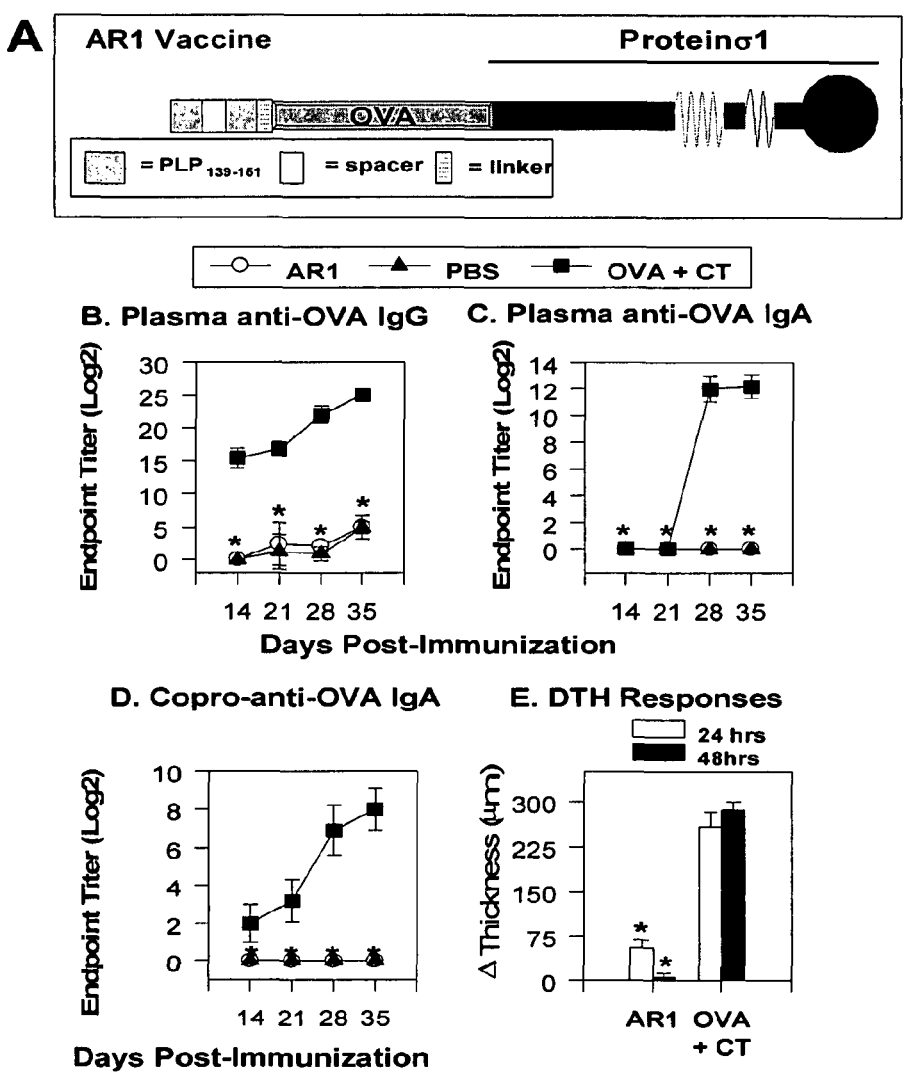

FIG. 9. Modification of OVA-pσ1 with encephalitogenic peptides retains ability to induce unresponsiveness to OVA. (FIG. 9A) OVA-pσ1 was genetically modified at its N-terminus to express 2 copies of the encephalitogenic peptide derived from proteolipid protein (PLP)$_{139-151}$ separated by an irrelevant peptide sequence ((MOG)$_{35-55}$); this fusion protein is referred to as AR1. (FIG. 9B-E) C57BL/6 mice were nasally dosed on days 0, 7, & 14 with 100 μg of AR1, and (FIG. 9B) plasma IgG and (FIG. 9C) IgA and (FIG. 9D) copro-IgA were measured by OVA-specific ELISA. Only the OVA+CT group showed anti-OVA Abs. *P<0.001. On days 21 and 27, mice were challenged i.n. with OVA+CT. Then on day 35, DTH test was performed as described in FIG. 3 (10 μg of OVA was injected into the left ear pinna and PBS alone into the right ear pinna as a control. Ear swelling was measured 24 and 48 hrs later, and differences recorded). Again, only the OVA+CT group showed a DTH response upon OVA challenge. Thus, these data show that the genetic fusion of the described peptides did not interfere with the OVA-pσ1 core.

Figure 10:
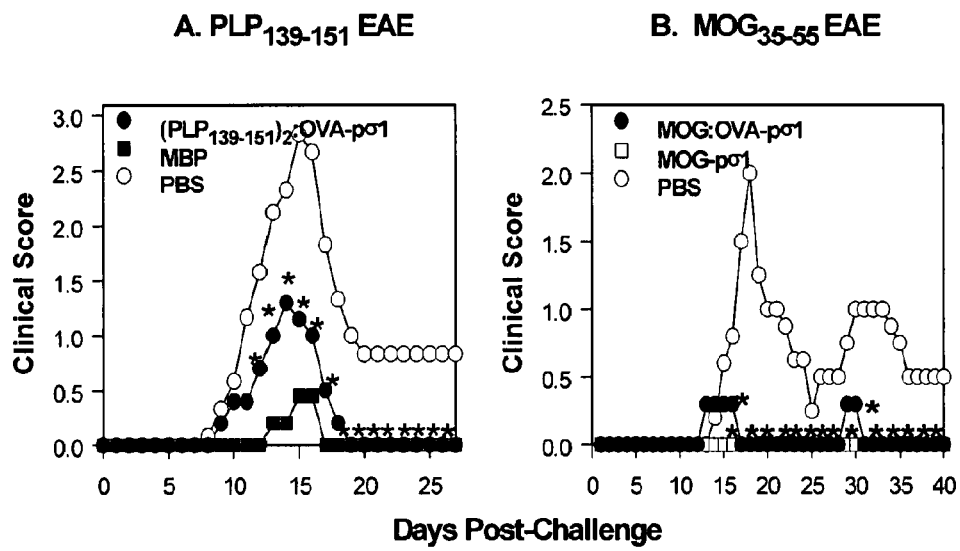

FIG. 10. Mice nasally dosed with AR1 (a tolerogenic vaccine for EAE) are protected against EAE challenge. (FIG. 10A) SJL/J mice were dosed with proteolipid protein peptide (PLP$_{139-151}$)$_2$:OVA-pσ1 (AR1; n=8), as described in FIG. 9, and were challenged s.c. with PLP$_{139-151}$ in modified complete Freund's adjuvant +i.p. pertussis toxin (PT). A second dose of PT was given i.p. two days later and mice were followed for disease. As a positive oral tolerance control (n=5), one group of mice was orally tolerized with myelin basic protein (MBP) since these mice were protected (p<0.001) as were mice dosed with AR1 (p<0.001) when compared to PBS-dosed (diseased) mice (n=8). (FIG. 10B) C57BL/6 mice were nasally dosed with 50 μg myelin oligodendrocyte glycoprotein$_{29-146}$ genetically fused to pσ1 (MOG-pσ1) or to OVA-pσ1 (MOG:OVA-pσ1) three times at weekly intervals, and then 1 wk after the last i.n. dose, mice were challenged s.c. with 150 μg MOG$_{35-33}$ on day 0 and 7 of challenge, and given i.v. PT on days 0 and 2. Both the MOG-pσ1 (n=5) and MOG:OVA-pσ1 (n=5) protected mice (p<0.001) when compared to PBS-dosed mice (n=5).

Figure 11:
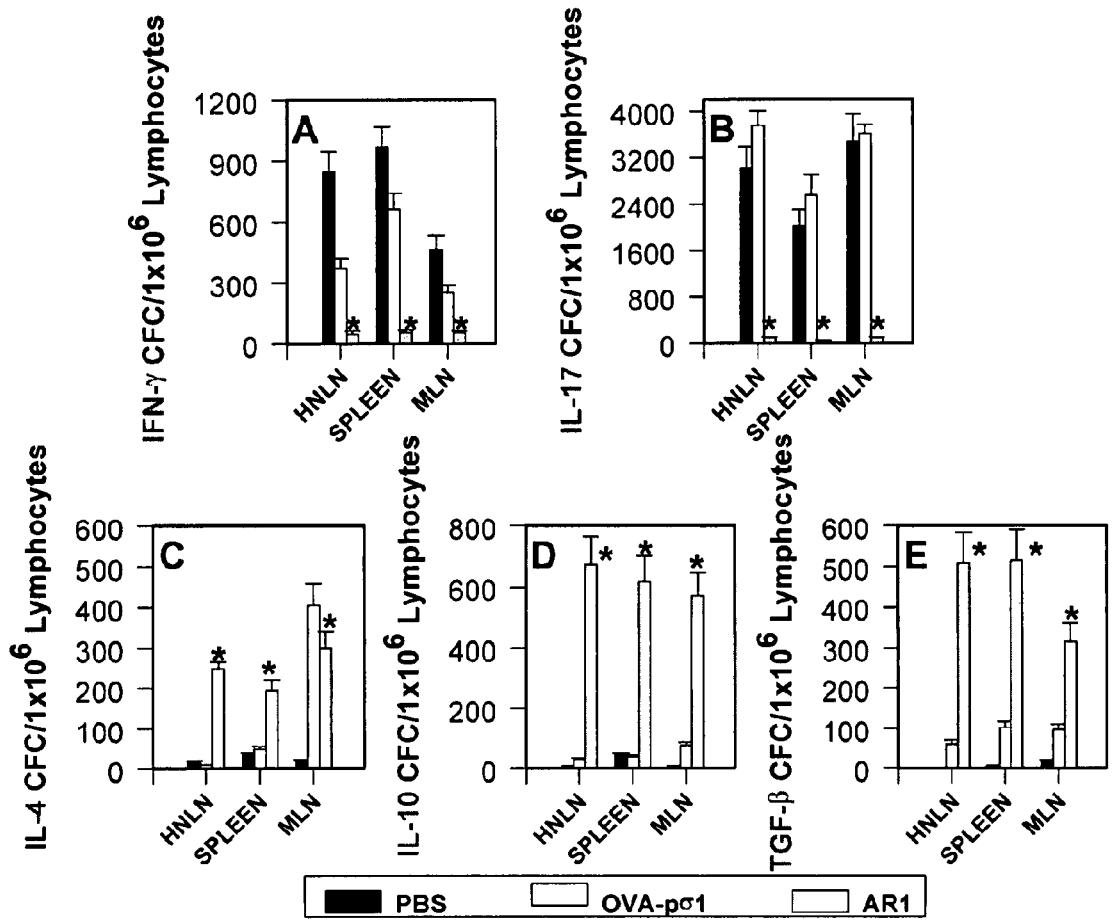

FIG. 11. Protection against PLP$_{139-151}$ challenge is attributed to the stimulation of the regulatory cytokines, IL-4, IL-10, and TGF-β. SJL mice were dosed with AR1, OVA-pσ1, or PBS as described in FIG. 9. Mice were then challenged with PLP$_{139-151}$ peptide as described in FIG. 10. HNLN, spleens, and MLN were harvested at peak of disease (day 14) and purified CD4$^+$ T cells were restimulated with PLP$_{139-151}$ peptide for 2 days, and evaluated in a cytokine ELISPOT. PBS- and OVA-pσ1-dosed (unprotected mice) showed elevated (FIG. 11A) IFN-γ and (FIG. 11B) IL-17 cytokine-forming cells (CFC), and no (FIG. 11C) IL-4, (FIG. 11D) IL-10, or (FIG. 11E) TGF-β CFC. In contrast, AR1-dosed (tolerized) mice showed elevated IL-4, IL-10, and TGF-β CFC and no IFN-γ or IL-17 CFC. Thus, only AR1 mice were protected against challenge, and tolerance induced to irrelevant protein (OVA-pσ1) did confer protection. *P<0.001 between AR1-dosed mice versus PBS-dosed mice.

Figure 12:
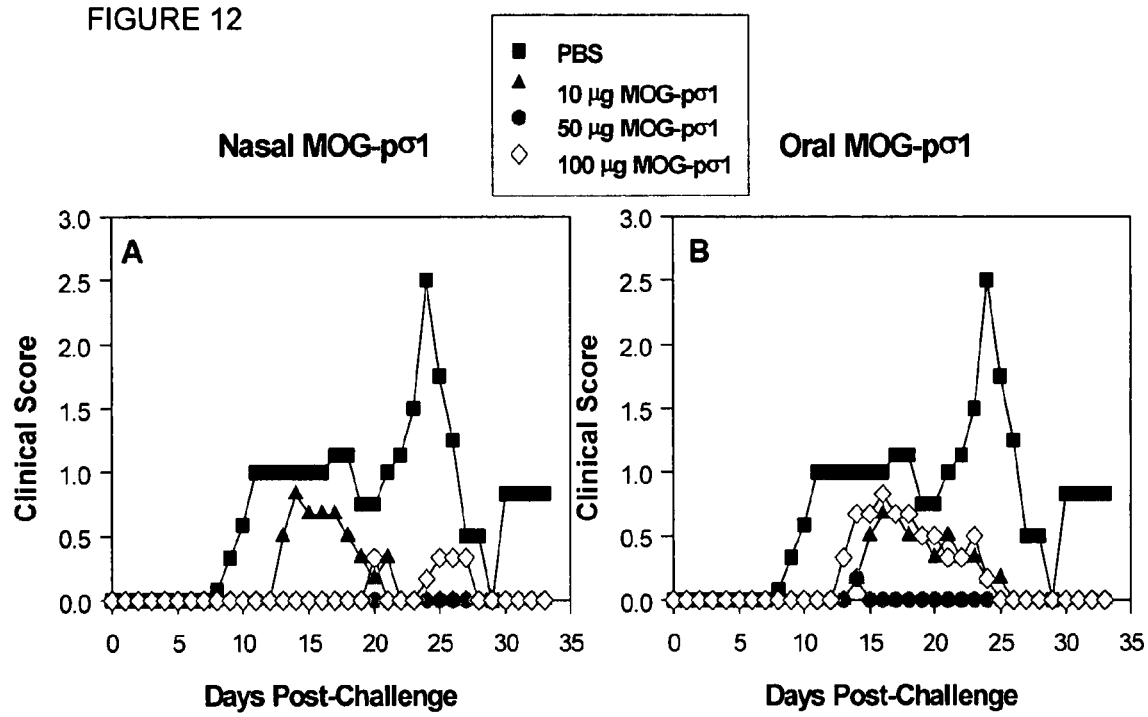

FIG. 12. Single nasal or oral dose with MOG-pσ1 protects C57BL/6 mice against challenge with MOG$_{35-55}$. Mice (5/group) were dosed once (FIG. 12A) nasally or (FIG. 12B) orally with 10, 50, or 100 μg of MOG$_{29-146}$-pσ1 (MOG-pσ1) or with PBS, and 10 days later challenged with MOG$_{35-55}$ per description for FIG. 10. In a dose-dependent fashion, protection against autoimmune challenge showed protection, but the 50 μg dose conferred the best protection with no disease, while minimal disease was observed at the 10 or 100 μg doses. Thus, pσ1 delivery is an effective means to deliver autoantigens to the mucosa for the development of tolerance to self antigens.

Figure 13:
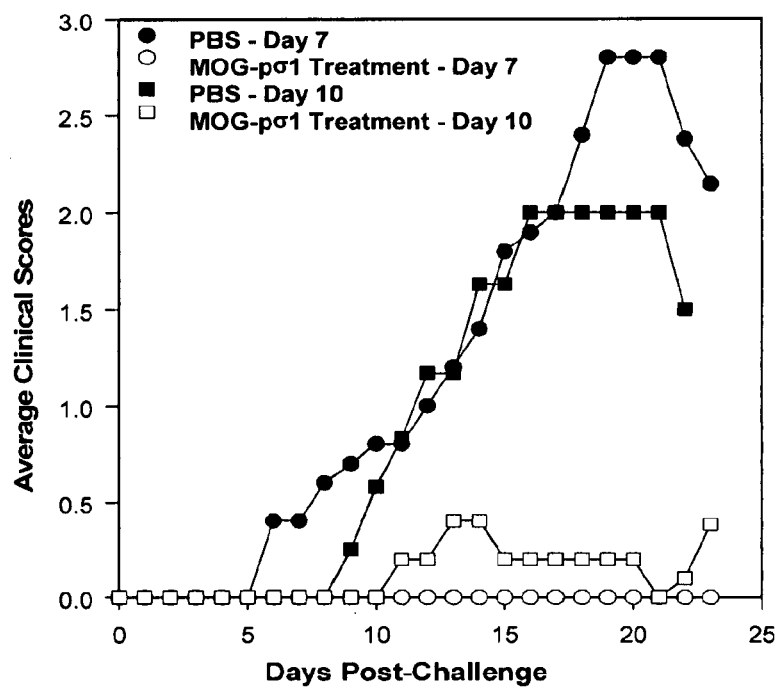

FIG. 13. Nasal treatment of C57BL/6 mice with MOG-pσ1 results in diminished EAE. Groups of C57BL/6 mice were induced with EAE as described in FIG. 10B using MOG$_{35-55}$ peptide. On day 7, one group of mice were nasally dosed with 50 μg MOG-pσ1 or PBS, and disease course followed. On days 10 and 17, separate groups of mice were nasally dosed with 50 μg MOG-pσ1, and disease course followed. Mice treated with MOG-pσ1 showed either no EAE or only minor disease in some mice. Thus, MOG-pσ1 can be used therapeutically to treat EAE.

BRIEF DESCRIPTION OF THE SEQUENCE LISTING

The nucleic and amino acid sequences listed in the accompanying sequence listing are shown using standard letter abbreviations for nucleotide bases, and three-letter code for amino acids, as defined in 37 C.F.R. §1.822. Only one strand of each nucleic acid sequence is shown, but as appropriate in context the complementary strand is understood as included by any reference to the displayed strand. In the accompanying sequence listing:

SEQ ID NO: 1 shows the nucleic acid sequence encoding adenovirus 2 fiber protein (HAD278923).

SEQ ID NO: 2 shows the protein sequence of adenovirus 2 fiber protein.

SEQ ID NO: 3 shows the nucleic acid sequence encoding reovirus type 3 sigma 1 (haemagglutinin) (RET3S1).

SEQ ID NO: 4 shows the amino acid sequence of reovirus type 3 sigma 1 (haemagglutinin).

SEQ ID NO: 5 shows the nucleic acid sequence encoding adenovirus 16 fiber protein (AX034843).

SEQ ID NO: 6 shows the amino acid sequence of adenovirus 16 fiber protein.

SEQ ID NO: 7 shows the nucleic acid sequence encoding adenovirus 35 fiber (fiber) protein (30827 to 31798 of BK005236).

SEQ ID NO: 8 shows the amino acid sequence of adenovirus 35 fiber protein (30827 to 31798 of BK005236).

SEQ ID NO: 9 shows the nucleic acid sequence encoding adenovirus 37 fiber protein (x94484).

SEQ ID NO: 10 shows the amino acid sequence of adenovirus 37 fiber protein (x94484).

SEQ ID NO: 11 shows the nucleic acid sequence (V00383) encoding ovalbumin.

SEQ ID NO: 12 shows the amino acid sequence of ovalbumin.

DETAILED DESCRIPTION

All publications and patent applications herein are incorporated by reference to the same extent as if each individual publication or patent application was specifically and individually indicated to be incorporated by reference (including those so indicated). The provided description includes information that may be useful in understanding the present invention. It is not an admission that any of the information provided herein is prior art or relevant to the presently claimed embodiments, or that any publication specifically or implicitly referenced is prior art. Although any methods and materials similar or equivalent to those described herein can be used in the practice or testing of the present invention, example methods and materials are described.

I. Abbreviations
  Ab, antibody
  AFC, Ab forming cells
  Ag, antigen
  CT, native cholera toxin
  GALT, gut-associated lymphoreticular tissues
  iLP, small intestinal lamina propria
  MLNs, mesenteric lymph nodes
  OVA, ovalbumin
  OVA-pσ1, OVA genetically fused to protein sigma one of reovirus
  PPs, Peyer's patches
  S-IgA, secretory-IgA
  Treg, regulatory T II. Terms Unless defined otherwise, all technical and scientific terms used herein have the meaning commonly understood by a person skilled in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments, the following explanations of specific terms are provided:

As used herein, the term "adjuvant" refers to a substance sometimes included in a vaccine formulation to enhance or modify the immune-stimulating properties of a vaccine.

As used herein, the term "antibody" refers to a large Y shaped protein molecule made by B-cells of the immune system which very selectively binds to other specific protein molecules called antigens.

As used herein, the term "antigen" refers to a foreign substance that that when introduced into the body triggers an immune system response, resulting in production of an antibody as part of the body's defense against disease.

As used herein, the term "DNA vaccine" refers to a eukaryotic expression system encoding the molecular machinery for the expression of the subunit vaccine encoded in plasmid nucleic acids.

As used herein, the term "expression" refers to the vaccine vector which is responsible for producing the vaccine.

As used herein, the term "immunization" refers to a process by which a person or animal becomes protected against a disease; the process of inducing immunity by administering an antigen (vaccine) to allow the immune system to prevent infection or illness when it subsequently encounters the infectious agent.

As used herein, the term "mucosal" means any membrane surface covered by mucous.

As used herein, "mucosal targeting ligand" refers to a viral protein or adhesins that specifically bind to the epithelia to enable uptake of the vaccine. These MTLs are not restricted to proteins, but can a protein derivatized or not with carbohydrates and/or lipids. Likewise, carbohydrate, lipid, or nucleic acids found to bind to the epithelia can also be included as mucosal targeting ligands. Methods for making MTLs and additional examples thereof are described in PCT/US2006/001346 (published as WO 2006/078567), which is incorporated herein by reference in its entirety.

As used herein, the term "toleragen" means any antigen (such as a protein, nucleic acid, carbohydrate, lipid, or combination of any thereof) that mediates host unresponsiveness. By way of example, a toleragen works by inducing the tolerized host not to produce antibodies or cell-mediated immune responses specific for the toleragen. Additional discussion of toleragens may be found, for instance, in PCT publication WO 2006/052668, which is incorporated herein in its entirety.

III. Tolerizing Agents

One of the problems for conventional tolerization regimens is the requirement to use high doses, or repeated dosing, of antigen (toleragen or allergen). This disclosure provides evidence that the addition of a targeting molecule (or tolerizing agent), represented in various embodiments by protein sigma 1 (pσ1), mediates tolerance after a single oral dose or with minimal dosing. This enables use of far less toleragen when it is genetically fused to pσ1. As an example, typically, 25 mg of toleragen (for instance, the test antigen used in this case, ovalbumin (OVA)) is required to be given twice orally in order to induce tolerance as measured by lack of proliferative T-cell responses to OVA, reduced anti-OVA antibody responses, and reduced delayed type hypersensitivity reactions. In contrast, a single, low oral dose (100 µg) of OVA-pσ1 fusion protein was sufficient to elicit tolerance. This indicates the fusion is at least 500-fold more effective than convention.

Given this finding, the addition of a targeting molecule that directs (targets) a toleragen to the host M cells and/or mucosal epithelium and/or host dendritic cells, mediates tolerance induction via binding to host sialic acid, specific host receptors, or via a combination of these or other mechanisms. Such binding events contribute in part or in whole to the eventual development of tolerance.

In addition to pσ1, other ligands that contribute to binding to M cells, dendritic cells, and/or mucosal epithelium and thereby mediate tolerance to a passenger molecule are included. As example, adenovirus 35 fiber protein or adenovirus 37 fiber protein, the latter of which has sialic acid binding activity and can also be used to elicit tolerance to a molecule fused or attached thereto. Any toleragen that can be fused to such (targeting) ligands, or adaption of such ligands for delivery of particles (e.g., nanoparticles, microspheres, liposomes, or virus-like particles), can be used to induce tolerance and thereby, for instance, prevent or treat autoimmune diseases, allergies, food allergies, or allow for tolerization to permit continued treatment with biologicals, e.g., botulinum neurotoxins (BoNTs).

Representative targeting molecules (or domains of molecules) that contribute to binding (e.g., to M cells, dendritic cells, and/or mucosal epithelium) include but are not limited to known viral proteins. Sequences of such proteins, and the nucleic acids encoding them, can be found in public databases, such as GenBank. For instance, in addition to specific sequences discussed herein in detail, another nucleotide sequence encoding a human adenovirus 2 fiber protein is found under Accession No. AJ278923. Similarly, an example reovirus 3 sigma 1 is found under Accession No. X01161.

By way of example, the fusion of the pσ1 or like (tolerizing) molecule to the heavy and/or light chain(s) of a BoNT allows the adaption of the resultant fusion protein as a prophylactic or therapeutic vaccine to prevent or treat immune reactivity against BoNT. BoNTs are currently used for a variety of treatments including tremor disorders. Consequently, repeated exposure to native BoNTs can result in the development of neutralizing antibodies to the BoNTs. Such exposure can prevent BoNT treatments. However, the use of a tolerizing molecule as described, in conjunction with BoNT light and/or heavy chains, can prevent or treat this immune reactivity. Thus, this disclosure describes the addition of mucosal targeting molecule(s) that enhance tolerance induction.

One embodiment of this present disclosure is that certain molecules that bind the mucosal epithelium can elicit tolerance in a subject. Thus, for example, using the reovirus protein σ1, a subject can be "vaccinated" for instance nasally, orally, or peripherally for tolerance induction, thereby preventing the host (subject) from reacting against the passenger antigen fused thereto. Evidence provided here shows that OVA-σ1, when given orally or nasally, makes the host unresponsive to OVA. In a similar fashion, when other protein or peptides are genetically engineered onto OVA-σ1 or pσ1, tolerance to autoimmune epitopes can also be induced. For example, peptides from mouse proteolipid protein or from myelin oligodendrocyte glycoprotein genetically engineered onto OVA-pσ1, when given, can reduce a multiple sclerosis-like disease. Thus, any components that induce human or animal autoimmune disease when fused to pσ1, and given to induce tolerance, should prevent or treat autoimmune diseases, such as multiple sclerosis, arthritis, diabetes, Hashimoto's disease, Graves' disease, Sjögren syndrome, etc.

Another embodiment is that compounds described herein can be used to induce tolerance to botulinum neurotoxins or other biological therapeutic agents. Currently, botulinum neurotoxins are used to treat tremor disorders as well as for cosmetic applications. However, one side-effect is that the individual can develop neutralizing antibodies resulting in the therapeutic loss of these treatments. Thus, an MTL fused to the β-trefoil vaccine, heavy chain, or the light chain to botulinum neurotoxins. Thus, this shows that drugs or therapeutics can be applied to pσ1, to limit the host response. These can also include host inflammatory mediators, e.g., cytokines or soluble cytokine receptors, such that the individual shows unregulated or elevated expression of these inflammatory mediators that need to be suppressed.

Also particularly contemplated are fusion proteins that contain a tolerizing ligand (or its sialic acid binding domain component) that targets the fusion protein to host M cells and/or mucosal epithelium and/or host dendritic cells, and a component or fragment of at least one botulinum neurotoxin from serotype A, B, C, D, E, F, or G that will induce tolerance to botulinum. In some specific examples, the fusion protein contains a component or fragment, or domain, from two or more serotypes, or in some instances from all of serotypes A through G.

Tolerizing antigens include, but are not limited to, autoimmune antigens ("autoantigens"), therapeutically active biological agents, allergens, inflammatory antigens, and so forth. By way of example, therapeutically active biological agents maybe any immunologically active (that is, immune stimulatory) proteins or peptides that have a therapeutic function, such as growth factors, hormones (e.g., insulin), clotting factors (e.g., Factor VIII), metabolic enzymes, therapeutic antibodies (e.g., HERCEPTIN® or Trastuzumab), toxins (e.g., botulinum toxin), and so forth. Additional specific antigens that could usefully be fused to a targeting portion in the described fusion proteins will be known to those of ordinary skill in the art. For instance, WO 2006/052668 describes a number of representative antigens and categories thereof that can be used for tolerization.

The fusion proteins described herein are useful as therapeutic compounds for treatment of subjects, including human and veterinary subjects. As demonstrated, routes of administration include oral and nasal application, though other routs are contemplated. The dosage form of a pharmaceutical composition comprising one or more of the provided tolerizing fusion proteins will be influenced by the mode of administration chosen. For instance, in addition to injectable fluids, inhalational, topical, opthalmic, peritoneal, and oral formulations can be employed. Inhalational preparations can include aerosols, particulates, and the like. In general, the goal for particle size for inhalation is about 1 μm or less in order that the pharmaceutical reach the alveolar region of the lung for absorption. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia);

non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the compounds for use according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

The pharmaceutical compositions that comprise at least one therapeutic agent, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The therapeutically effective amount of therapeutic agent, and specifically a tolerizing fusion protein, will be dependent on the specific fusion protein utilized, the subject being treated, the severity and type of the affliction, and the manner of administration. The exact dose is readily determined by one of skill in the art based on the teachings herein, along with the potency of the specific compound, the age, weight, sex and physiological condition of the subject. By way of example, in various embodiments the dosage of a tolerizing fusion protein required to achieve (or maintain) tolerance in a subject is low relative to traditional tolerization regimens. For instance, as few as one or a few doses (e.g., fewer than about three, or fewer than about five doses) of agent may be sufficient to induce tolerance. Similarly, a relatively low amount of antigen is required per dose, compared to previously known tolerance approaches). By way of example, as little as 1 mg or less of antigen in a dose (or total, in a series of doses) will be effective with some fusion proteins. In other instances, as little as 500 µg, 300 µg, 250 µg, or less in a dose, or total in a series of doses, or even as little as 200 µg, 150 µg, 100 µg, or less will be effective. Based on, and the skill of practitioners who engage in tolerance induction, specific dosages and dosage regimens can readily be worked out for any particular tolerizing fusion protein using the teachings herein.

Ovalbumin-Protein σ1 M Cell Targeting Enhances Oral Tolerance with Loss of OVA-Specific $CD4^+$ T Cells In this example, facilitated induction of oral tolerance using an M cell-targeting protein antigen delivery system was examined. Mice were fed different doses of (1) a recombinant protein sigma one (pσ1) of reovirus genetically conjugated to ovalbumin (OVA-pσ1) described herein or (2) PBS prior to oral challenge with OVA plus cholera toxin as mucosal adjuvant. A low dose of OVA-pσ1 reduced anti-OVA antibody and CD4-positive ($CD4^+$) T cell responses in both mucosal and systemic lymphoid tissues. OVA/MHC II-$A^d$ tetramer staining revealed that the numbers of OVA-specific $CD4^+$ T cells were significantly more reduced in the small intestinal lamina propria (iLP) of mice fed OVA-pσ1 than of those fed PBS, while no significant difference was seen for the spleen. The spleen of orally tolerized mice showed an increased frequency of $CD25^+$, $CD4^+$ T cells with TGF-β1 production. These results show that mucosal and systemic unresponsiveness are regulated by distinct T cell subsets.

Experimental Procedures

Mice

BALB/c mice were purchased from the Frederick Cancer Research facility (Frederick, Md.). Mice were housed in microisolators, maintained in horizontal laminar flow cabinets, and provided sterile food and water as part of a specific-pathogen-free facility in the Immunobiology Vaccine Center at the University of Alabama at Birmingham. The health of the mice was monitored by both serology for bacterial and viral pathogens and immunohistology. All of the mice used in these experiments were free of bacterial and viral pathogens.

Construction of OVA-pσ1 for M Cell Targeting

PCR was used to obtain the cloned pσ1 cDNA from reovirus serotype 3 strain Dearing as previously described (Wu et al., Gene Ther. 7:61-69, 2000). Ovalbumin (OVA) was genetically fused to pσ1's N-terminus and is referred to as OVA-pσ1. The OVA-pσ1 was produced using a Pichia pastoris yeast expression system as a his-tag labeled protein.

Oral Immunization

Mice were gastrically intubated with different doses of OVA-pσ1 dissolved in 0.25 ml of PBS. Control mice received PBS only. Seven days later, mice were orally immunized with 1 mg of OVA plus 15 µg of CT three times at weekly intervals (Kato et al., J. Immunol. 166:3114-3121, 2001). OVA-specific T and B cell responses were determined seven days after the last immunization (Kato et al., J. Immunol. 166:3114-3121, 2001).

OVA-specific Antibody Assays

OVA-specific antibody (Ab) levels in plasma and mucosal secretions were determined by an ELISA as previously described (Kato et al., J. Immunol. 166:3114-3121, 2001; Kato et al., Int. Immunol. 15:145-158, 2003; Fujihashi et al., Proc. Natl. Acad. Sci. (USA) 98:3310-3315, 2001; Hagiwara et al., J. Immunol. 170:1754-1762, 2003; Kataoka et al., J. Immunol. 172:3612-3619, 2004). Briefly, 96-well FALCON™ microtest assay plates (BD BioSciences, Oxnard, Calif.) were coated with one mg/ml of OVA in PBS. After blocking with 1% BSA in PBS, two-fold serial dilutions of samples were added to each well. Following incubation overnight at 4° C., horseradish peroxidase (HRP)-labeled goat anti-mouse µ, γ or α heavy chain-specific Abs (Southern Biotechnology Associates (SBA), Birmingham, Ala.) were added to wells. The color reaction was developed for fifteen min at room temperature with 100 µl of 1.1 mM 2, 2'-azino bis (3-ethylbenz-thiazoline-6-sulfonic acid) in 0.1 M citrate phosphate buffer (pH 4.2) containing 0.01% $H_2O_2$. Endpoint titers were expressed as the reciprocal $log_2$ of the last dilution that gave an optical density at 415 nm of 0.1 greater than background.

Lymphoid Cell Isolation and Enumeration of Ab-forming Cells

The spleen and MLNs were removed aseptically and single-cell suspensions prepared in RPMI 1640 (Cellgro Mediatech, Washington, D.C.) containing HEPES buffer, non-essential amino acids, sodium pyruvate, L-glutamine, penicillin, streptomycin and gentamycin (incomplete medium) by passage through sterile wire mesh screens as described previously (Kato et al., J. Immunol. 166:3114-3121, 2001; Fujihashi et al., Proc. Natl. Acad. Sci. (USA) 98:3310-3315, 2001). Peyer's patches (PPs) were carefully excised from the small intestinal wall and dissociated using the neutral protease enzyme collagenase type IV (Sigma) in incomplete RPMI 1640 to obtain single-cell preparations (Kato et al., *J. Immunol.* 166:3114-3121, 2001, Kato et al., *Int. Immunol.* 15:145-158, 2003). Mononuclear cells in the iLP were isolated after removal of PP and intraepithelial lymphocytes from the small intestine using a combination of enzymatic dissociation and discontinuous PERCOLL™ density gradients (Pharmacia Fine Chemicals, Uppsala, Sweden). Mononuclear cells in the interface between the 40% and 75% layers were removed, washed and resuspended in RPMI 1640 containing 10% FCS (complete RPMI 1640) (Kato et al., *J. Immunol.* 166:3114-3121, 2001; Fujihashi et al., *Proc. Natl. Acad. Sci.* (*USA*) 98:3310-3315, 2001). Mononuclear cells obtained from mucosal and systemic lymphoid tissues were subjected to an ELISPOT assay in order to detect numbers of OVA-specific Ab-forming cells (AFCs) (Kato et al., *J. Immunol.* 166:3114-3121, 2001; Kato et al., *Int. Immunol.* 15:145-158, 2003; Fujihashi et al., *Proc. Natl. Acad. Sci.* (*USA*) 98:3310-3315, 2001; Fujihashi et al., *J. Exp. Med.* 183:1929-1935, 1996; Hagiwara et al., *J. Immunol.* 170: 1754-1762, 2003; Kataoka et al., *J. Immunol.* 172:3612-3619, 2004). Briefly, 96-well nitrocellulose plates (Millititer HA; Millipore, Bedford, Mass.) were coated with one mg/ml of OVA for analysis of anti-OVA-specific AFCs. The numbers of OVA-specific AFCs were quantified using an IMMUNO-SPOT® spot analyzer Analyzer (Cellular Technology Ltd., Cleveland, Ohio) (Hagiwara et al., *J. Immunol.* 170:1754-1762, 2003; Kataoka et al., *J. Immunol.* 172:3612-3619, 2004).

Delayed Type Hypersensitivity (DTH) Responses

OVA-specific DTH responses were measured 7 days after the last oral challenge with OVA plus CT, as described above. Briefly, PBS (20 µl) containing 10 µg of OVA was injected into the left ear pinna of mice while the right ear pinna received a PBS control injection (Kato et al., *J. Immunol.* 166:3114-3121, 2001; Fujihashi et al., *Acta. Odontol. Scand.* 59:301-308, 2001; Kato et al., *Int. Immunol.* 15:145-158, 2003). Ear swelling was measured 24 hours later with a dial thickness gauge (Ozaki Manufacturing Co., Ltd., Tokyo, Japan). The DTH response was expressed as the increase in ear swelling after OVA injection minus the swelling in the PBS-injected control site.

Ag-specific T Cell Responses

CD4$^+$ T cells from spleen, MLNs, and PPs were purified by use of an automated magnetic activated cell sorter (AUTOMACS™) system (Miltenyi Biotec, Auburn, Calif.), as described previously (Hagiwara et al., *J. Immunol.* 170:1754-1762, 2003; Kataoka et al., *J. Immunol.* 172:3612-3619, 2004). Briefly, a nylon wool column of an enriched T cell fraction was incubated with biotinylated anti-CD4 mAb (GK 1.5) (BD PharMingen) followed by streptavidin-conjugated microbeads and sorted to purity with the AUTOMACS™. This purified T cell fraction was >97% CD4$^+$ and the cells were >99% viable. The purified CD4$^+$ T cell fraction was then resuspended in complete RPMI 1640 (4×10$^6$ cells/ml) and cultured in the presence of one mg/ml OVA of cultures of T cell-depleted, irradiated (3000 rad) splenic antigen-presenting cells taken from non-immunized, normal mice. To assess OVA-specific T cell proliferative responses, an aliquot of 0.5 µCi of tritiated [$^3$H]-TdR (Amersham Biosciences, Arlington Heights, Ill.) was added during the final 18 hour of incubation, and the amount of [$^3$H]-TdR incorporation was determined by scintillation counting. The supernatants of identically treated T cell cultures not incubated with [$^3$H]-TdR were then subjected to a cytokine-specific ELISA as described below.

Cytokine-Specific ELISA

Levels of cytokines in culture supernatants were measured by an ELISA. The details of the ELISA for IFN-β, IL-2, IL-4, IL-5, IL-6 and IL-10 have been described previously (Kato et al., *J. Immunol.* 166:3114-3121, 2001; Kato et al., *Int. Immunol.* 15:145-158, 2003; Fujihashi et al., *Proc. Natl. Acad. Sci.* (*USA*) 98:3310-3315, 2001; Hagiwara et al., *J. Immunol.* 170:1754-1762, 2003; Kataoka et al., *J. Immunol.* 172:3612-3619, 2004). The following were used as coating and detection mAbs, respectively: anti-IFN-β: R4-6A2 and XMG 1.2 mAbs; anti-IL-2: JES6-1A12 and JES6-5H4 mAbs; anti-IL-4: BVD4-1D11 and BVD6-24G2 mAbs; anti-IL-5: TRFK-5 and TRFK-4 mAbs; anti-IL-6: MP5-20F3 and MP5-32C11 mAbs; and anti-IL-10: JES5-2A5 and JES5-16E3 mAbs. A mouse TGF-β1 immunoassay kit, QUANTIKINE™(R & D systems, Minneapolis, Minn.), was used to detect TGF-β1 in the culture supernatants. The levels of Ag-specific cytokine production were calculated by subtracting the results of control cultures (e.g., without Ag stimulation) from those of Ag-stimulated cultures. This ELISA was capable of detecting 0.8 ng/ml of IFN-β; 0.4 U/ml of IL-2; 25 pg/ml of IL-4; 0.8 U/ml of IL-5; 200 pg/ml of IL-6; 4 pg/ml of IL-10; and 4 pg/ml of TGF-β1.

Flow Cytometry Sorting and Analysis

In order to determine the frequencies of OVA-specific CD4$^+$ T cells, mononuclear cells from spleen, MLNs, PPs and iLP were stained with FITC-conjugated anti-CD4 (GK1.5), biotinylated anti-CD25 (7D4) mAb and PE-labeled OVA/MHC II-A$^d$ tetramer followed by Cy5.5-streptavidin before being subjected to flow cytometric analysis. For intracellular IL-10 analysis, cells were incubated with ionomycin (1 µg/ml, SIGMA, St. Louis, Mo.) and phorbol 12-myristate 13-acetate (PMA, 25 ng/ml, SIGMA) for 6 hours and then stained with PE-labeled anti-CD4, biotinylated anti-CD25 mAbs followed by Cy5.5-streptavidin. These samples were further stained intra-cellularly with ALEXA FLUOR® 488 labeled anti-IL-10 mAb (JES5-16E3). In some experiments, cells were stained with FITC-labeled anti-CD4 and biotinylated anti-CD25 mAb followed by PE-streptavidin. CD4$^+$ CD25$^+$ T cells were purified by flow cytometry and their TGF-β1 production was determined as described above.

Statistics

The significance of the difference (e.g., p values) among groups was evaluated by the Mann Whitney U test using a Statview II program designed for Macintosh computers.

Results

Optimization of Oral Doses of OVA-pσ1

Since it has been shown that pσ1 can bind to mucosal M cells (Wu et al., *Proc. Natl. Acad. Sci.* (*USA*) 98:9318-9323, 2001), it can be hypothesized that oral tolerance can be effectively achieved by OVA-pσ1. To test this notion, mice were gastrically intubated with different doses of OVA-pσ1. Mice were fed one dose of either 100 µg, 500 µg or 1000 µg of OVA-pσ1. An additional group of mice was given three daily doses of 100 µg of oral OVA-pσ1. Seven days later, all groups of mice were challenged once a week for three weeks with oral OVA plus CT. OVA-specific plasma IgG Ab titers were not markedly reduced in mice given three weekly doses of 100 µg of OVA-pσ1 (FIG. 1). On the other hand, they were significantly more reduced in all other single OVA-pσ1 treatment groups than in mice fed PBS (FIG. 1). Further, OVA-specific plasma IgA and mucosal S-IgA Ab responses in mouse groups receiving one feeding of OVA-pσ1 were markedly lower than in the positive control group (PBS-fed mice) (FIG. 1). These results show that a single oral dose of OVA-pσ1 effectively induces both systemic and mucosal unresponsiveness to OVA. Based upon these results, we next employed a single oral dose of 100 μg of OVA-pσ1 for further experiments.

Oral OVA-pσ1 Facilitates Both Systemic and Mucosal Unresponsiveness

Figure 2:
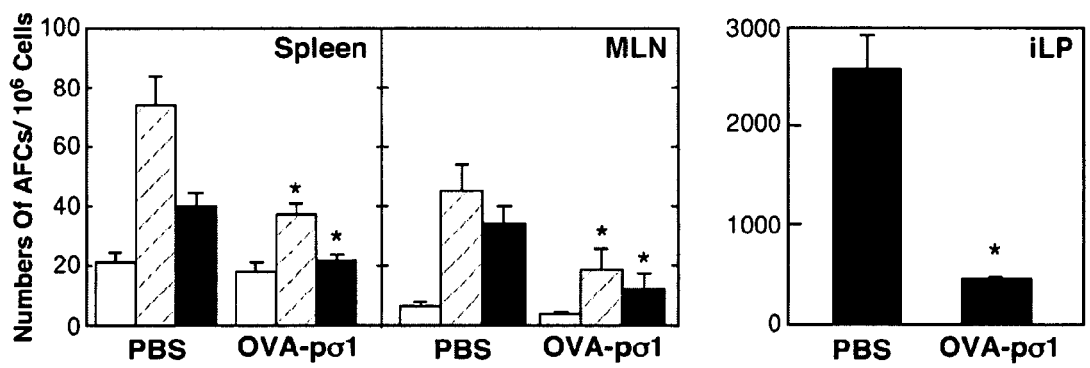

To further confirm these findings at the cellular level, the numbers of OVA-specific Ab-forming cells (AFCs) were examined in various lymphoid tissues of mice given oral OVA-pσ1 or PBS. Numbers of OVA-specific IgG and IgA AFCs in spleen and mesenteric lymph nodes (MLNs) were reduced significantly (p<0.05) in the oral pσ1-group but not in the oral PBS-Group (FIG. 2), showing that oral tolerance is indeed induced by feeding 100 μg of OVA-pσ1. In order to assess induction of unresponsiveness in mucosal effector sites, the numbers of OVA-specific AFCs in iLP were compared in groups fed PVA-pσ1 or PBS. The number of anti-OVA IgA AFCs was reduced in the pσ1—but not the PBS-fed group (FIG. 2). These results suggest that M cell targeting by OVA-pσ1, Th1- and Th2-type cytokine production by OVA-stimulated CD4+ T cells was examined. Purified CD4+ T cells from the spleen and PPs of mice fed OVA or PBS were incubated with or without 1 mg of OVA in the presence of autologous APCs for five days. When the culture supernatants were harvested and examined by cytokine-specific ELISA, OVA-pσ1-fed mice showed reduced CD4+ Th1 (IFN-γ and IL-2) and Th2 (IL-4, IL-5, IL-6 and IL-10) cytokine responses, while mice fed oral PBS showed high levels of Th2-type cytokines, especially IL-4 and IL-10 (Table 1). A virtually identical profile of up-regulation of Th2-type cytokine synthesis was seen in the spleen of mice following oral administration of PBS. On the other hand, a hyporesponsive Th1- and Th2-type cytokine profile was noted in both PPs and spleen of mice fed OVA-pσ1 before being orally challenged with OVA plus CT (Table 1). Taken together, these results indicate that CD4+ T cell unresponsiveness was induced in both spleen and PPs by a single oral dose of OVA-pσ1.

TABLE 1

CD+Th1 and Th2 Cytokine Synthesis by OVA-Specific CD4+ T Cells[a]

| Lymphoid Tissue | Orally Immunized with | Th1 type[b] | | Th2 type[b] | | | |
|---|---|---|---|---|---|---|---|
| | | IFN-γ (ng/ml) | IL-2 (ng/ml) | IL-4 (pg/ml) | IL-5 (ng/ml) | IL-6 (ng/ml) | IL-10 (ng/ml) |
| Spleen | PBS | 5.9 ± 1.3[c] | 0.9 ± 0.18 | 477 ± 2.6 | 4.54 ± 0.2 | 1.28 ± 0.05 | 44.5 ± 2.9 |
| | OVA-pσ1 | 0.3 ± 0.02[e] | 0.19 ± 0.02[f] | 30 ± 0.8[e] | 0.18 ± 0.02[e] | 0.07 ± 0.02[e] | 1.8 ± 0.3[e] |
| Peyer's Patches | PBS | 4.2 ± 1.7 | 1.6 ± 0.05 | 420 ± 3.0 | 3.1 ± 0.2 | 0.8 ± 0.08 | 40.8 ± 1.1 |
| | OVA-pσ1 | 0.3 ± 0.03[e] | 0.15 ± 0.01 | 110 ± 1.1[f] | 0.27 ± 0.02* | 0.12 ± 0.01[f] | 2.2 ± 0.2[e] |

[a]Splenic CD4+ T cells (2 × 10^6/ml) from each group of mice were cultured with 1 mg/ml of OVA in the presence of T cell-depleted and irradiated splenic feeder cells (4 × 10^6/ml).
[b]Culture supernatants were harvested after 5 days (2 days for IL-2) of incubation and analyzed by the cytokine-specific ELISA.
[c]The results represent the mean ± one SEM of one of three separate experiments.
[d]N.D. indicate not detected.
[e]p < 0.01,
[f]p < 0.05 compared with PBS group.

OVA-pσ1 effectively induces mucosal tolerance and may contribute to the maintenance of mucosal homeostasis.

DTH and CD4+ T Cell Proliferative Responses

Whether tolerance was induced at the T cell level after a single oral dose of OVA-pσ1 was next determined. OVA-specific delayed-type hypersensitivity (DTH) responses were assessed in mice given either OVA-pσ1 or PBS orally. OVA-specific DTH responses were much more pronounced in the pσ1-group than in the PBS group (FIG. 3A), showing that OVA-specific T cell responses were tolerized by a single low dose of OVA-pσ1. Using the described oral challenge system, which allows examination of CD4+ T cell responses in mucosal lymphoid tissues, CD4+ T cell proliferative responses were next examined in both mucosal (MLNs and PPs) and systemic (spleen) compartments of mice given oral OVA-pσ1. The CD4+ T cells from spleen, PPs, and MLNs were purified by use of an automated magnetic-activated cell sorter (AUTOMACS™) system. These purified CD4+ T cell fractions were cultured with or without one mg/ml of OVA in the presence of T cell-depleted, irradiated splenic APCs taken from non-immunized, normal mice. Significant reductions in T cell proliferative responses were seen in the spleen, MLNs and PPs of the OVA-pσ1—but not the PBS-fed group (FIG. 3B). These results show that T cell unresponsiveness was initiated in mucosal inductive tissues such as the PPs, by M cell targeting of OVA-pσ1. Subsequently, these tolerized CD4+ T cells migrated into the spleen via the MLNs.

Cytokine Production by OVA-Stimulated CD4+ T Cells

Figure 4:
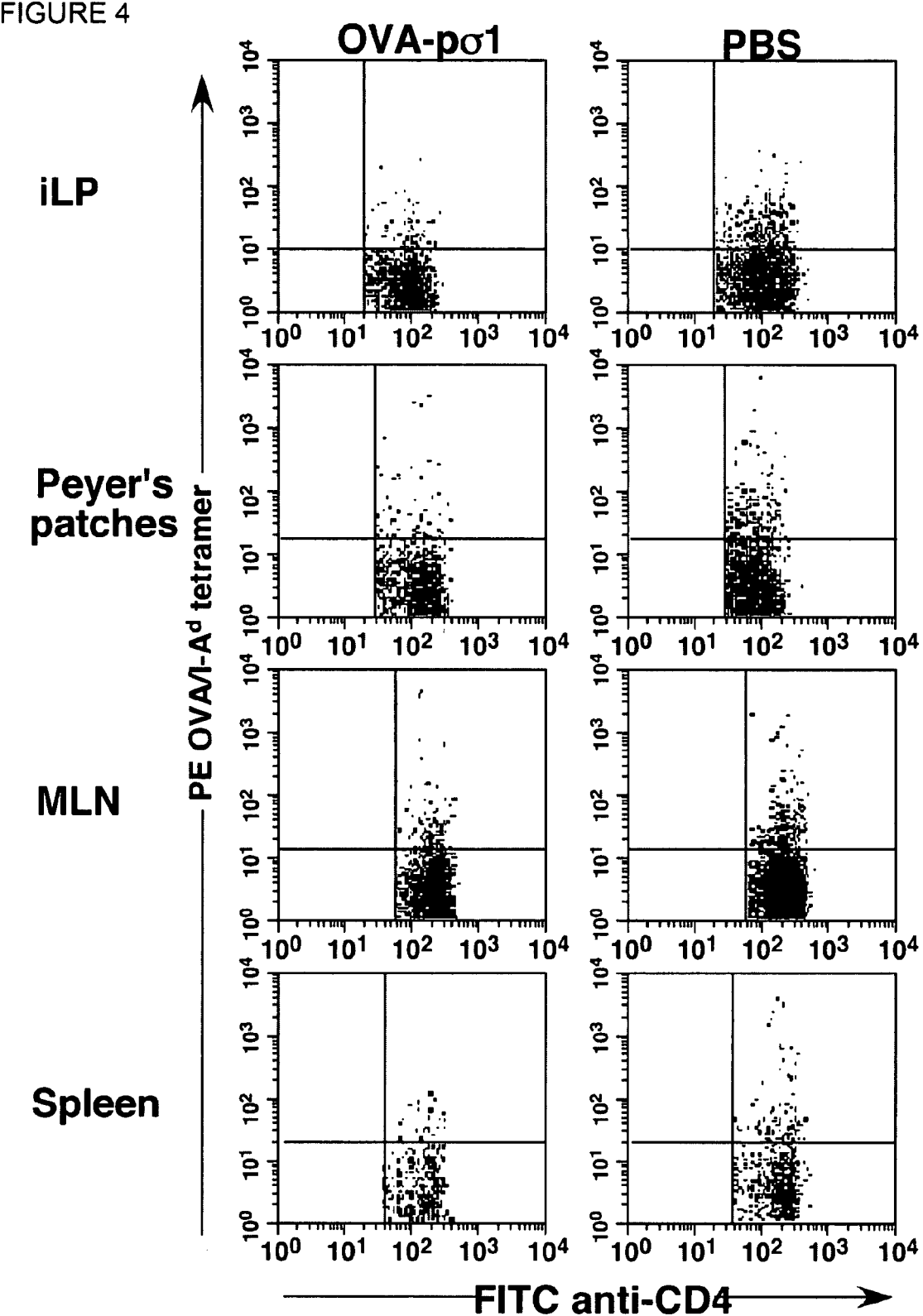

Since T cell unresponsiveness was induced in both systemic and mucosal lymphoid tissues by a single oral dose of Mucosal Unresponsiveness is Due to Clonal Deletion of OVA-Specific CD4+ T Cells In order to examine the role of OVA-specific CD4+ T cells in oral tolerance, mononuclear cells from spleen, PPs, MLNs and iLP were isolated one week after the last immunization and stained with FITC-conjugated anti-CD4, biotin-conjugated anti-CD25 mAbs and PE-labeled OVA/II-A[d] tetramer followed by Cy5.5-streptavidin. This analysis revealed a lower frequency of tetramer+ OVA-specific CD4+ T cells in iLPs of mice given OVA-pσ1 prior to oral challenge with OVA plus CT than in mice given oral PBS (FIG. 4 and Table 2). Numbers of OVA-specific CD4+ T cells were reduced in PPs and MLNs of mice given oral PVA-pσ1 (Table 2), but remained essentially the same in the spleen of orally tolerized mice and of those exhibiting high OVA-specific Ab titers (Table 2). When CD25 expression on tetramer+ OVA-specific CD4+ T cells was examined, the frequency of CD4+ CD25+ T cells was found to be significantly decreased in iLP of orally tolerized mice (Table 2). In addition, the numbers of tetramer+ OVA-specific CD4+ CD25− T cells in spleen, MLNs, PPs and iLP were also significantly reduced. Among these lymphoid tissues, marked reductions in OVA-specific CD4+ CD25− T cells were seen in the iLP of orally tolerized mice (Table 2). On the other hand, increased numbers of CD4+ CD25+ T cells, especially of the OVA/II-A[d] tetramer negative subset, were noted in spleen and MLNs of mice give oral PVA-pσ1 before mucosal challenge with OVA plus CT (Table 2). These results suggest that mucosal unresponsiveness to orally delivered Ag is most likely due to the reduced numbers of OVA-specific CD4+ T cells in the iLP (clonal deletion), a mechanism that is entirely distinct from the systemic unresponsiveness induced by active suppression by CD4+ CD25+ Treg cells.

TABLE 2

The frequency of OVA-specific CD4+ T cells in various lymphoid tissues[a]

| Lymphoid Tissue | Orally Immunized With | CD4+ (100%) | | |
|---|---|---|---|---|
| | | OVA/I-A$^d$ Tetramer+ CD25+ | OVA/I-A$^d$ Tetramer+ CD25+ | OVA/I-A$^d$ Tetramer− CD25+ |
| Spleen | PBS | 4.6 ± 0.4 | 5.1 ± 0.5 | 8.2 ± 0.4 |
| | OVA-pσ1 | 5.6 ± 1.1 | 3.6 ± 0.6[c] | 12.0 ± 0.8 |
| MLNs | PBS | 1.6 ± 0.3 | 2.8 ± 0.1 | 5.6 ± 1.1 |
| | OVA-pσ1 | 1.8 ± 0.3 | 2.0 ± 0.2[b] | 8.6 ± 1.0[d] |
| Peyer's patches | PBS | 2.6 ± 0.3 | 5.9 ± 0.6 | 6.3 ± 1.8 |
| | OVA-pσ1 | 2.7 ± 0.7 | 4.2 ± 0.5 | 5.2 ± 1.1 |
| Intestinal lamina propria | PBS | 1.9 ± 0.3 | 2.7 ± 0.2 | 4.5 ± 0.4 |
| | OVA-pσ1 | 0.8 ± 0.2[b] | 1.4 ± 0.1[b] | 2.9 ± 0.4 |

[a] Mononuclear cells (1 × 10$^6$) from various lymphoid tissues of mice fed OVA-pσ1 or PBS were stained with FITC-conjugated anti-CD4 (GK 1.5) and biotinylated anti-CD25 (7D4) mAbs as well as PE-labeled OVA/I-A$^d$ tetramer followed by Cy5.5-streptavidin. Samples were then subjected to flow cytometry analysis using FASCalibur ™. The results represent the mean values ± one SEM from these separate experiments.
[b] $p < 0.01$.
[c] $p < 0.03$
[d] $p < 0.05$ compared with PBS-group.

TGF-β1-Producing Treg Cells Are Induced by Oral OVA-pσ1

Figure 5:
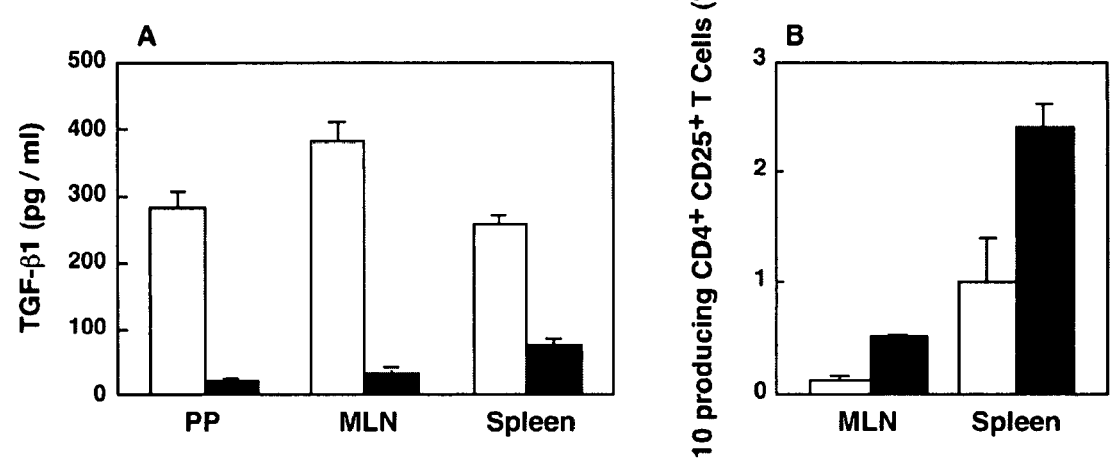

The increased frequency of CD4+ CD25+ T cells in spleen and MLNs suggested the possibility that CD4+ Treg cells are induced when mice are fed OVA-pσ1 and then mucosally challenged with OVA plus CT as mucosal adjuvant. To test this possibility, we examined the production of IL-10 and TGF-β1 by CD4+ CD25+ T cells. Flow cytometry-purified CD4+ CD25+ T cells from PPs, spleen and MLNs of mice fed OVA-pσ1 or PBS were stimulated with OVA for 5 days. The culture supernatants of CD4+ CD25+ T cells from orally tolerized mice contained higher levels of TGF-β1 than did those from PBS-fed mice (FIG. 5A). Intracellular IL-10 analysis was performed to determine the extent of IL-10 production by CD4+ CD25+ Treg cells in spleen and MLNs of orally tolerized mice. Flow cytometric analysis revealed fewer IL-10-producing CD4+ CD25+ T cells in mice fed OVA-pσ1 than in mice fed PBS (FIG. 5B). These results demonstrate that TGFβ1-producing CD4+ Treg cells were induced in the MLNs and spleen of mice fed OVA-pσ1.

Discussion

The current study shows that the OVA-pσ1 M cell-targeting delivery system facilitates the induction of oral tolerance. Mucosal and systemic unresponsiveness can be induced with a single oral dose of 100 μg of OVA-pσ1 instead of the repeated low doses of oral OVA that would otherwise be required. OVA-specific mucosal S-IgA and plasma IgG Ab responses as well as DTH and T cell proliferative responses were all reduced significantly in OVA-pσ1—but not in PBS-fed mice. Further, OVA-stimulated CD4+ T cells from spleen and PPs of orally tolerized mice showed much more marked reduction in the levels of both Th1- and Th2-type cytokine production than did those fed PBS before being orally challenged with OVA plus CT as adjuvant. The use of OVA/MHC II-A$^d$ tetramer staining revealed significantly reduced numbers of OVA-specific CD4+ T cells in iLP of mice fed OVA-pσ1. On the other hand, the numbers of TGF-β1-producing CD4+ CD25+ T cells were higher in the MLNs and spleen of orally tolerized mice than in the control group. These results show that the M cell-targeting Ag delivery by OVA-pσ1 feeding effectively induces mucosal and systemic unresponsiveness. Of key importance is the finding that the mechanisms regulating tolerance in mucosal and peripheral lymphoid tissues are distinct.

The M cells are known to take up and transport lumenal Ags, including proteins, viruses, bacteria, small parasites, and microspheres (Ermak et al., *Cell Tissue Res.* 279:433-436, 1995; Neutra et al., *Cell* 86:345-348, 1996; Gebert et al., *Int. Rev. Cytol.* 167:91-159, 1996; Wolf & Bye, *Annu. Rev. Med.* 35:95-112, 1984). M cells have then been shown to deliver the intact Ag into underlying lymphoid tissue of the GALT (Gebert et al., *Int. Rev. Cytol.* 167:91-159, 1996; Wolf & Bye, *Annu. Rev. Med.* 35:95-112, 1984). M cells are also thought to be involved in Ag processing and presentation, since the GALT M cells express MHC class II molecules and acidic endosomal-lysosomal compartments (Allan et al., *Gastroenterology* 104:698-708, 1993). In addition to serving as a means of transport for lumenal Ags, the M cells also provide an entryway for pathogens. For example, invasive strains of *Salmonella typhimurium* initiate murine infection by invading the M cells of the PPs (Jones et al., *J. Exp. Med.* 180:15-23, 1994). Based upon these findings, M cell-targeting Ag delivery could be assumed to be the normal pathway for induction of Ag-specific immune responses. Indeed, NALT M cell targeting a DNA vaccine constructed with pσ1 elicited Ag-specific IgG and S-IgA Ab responses (Wu et al., *Proc. Natl. Acad. Sci.* (*USA*) 98:9318-9323, 2001). However, our current study has now shown that oral administration of OVA-pσ1 facilitates unresponsiveness to OVA in both systemic and mucosal lymphoid tissues instead of inducting OVA-specific immunity. These opposite outcomes can be partially explained by the nature of the Ag. Ovalbumin is only weakly immunogenic and always requires an adjuvant for induction of immune responses. In contrast, cytomegalovirus plasmid DNA (pCMV), a known ligand for toll-like receptor 9, is recognized by IFN-γ producing cells and dendritic cells (Krug et al., *Immunity* 21:107-119, 2004) and most likely induces innate and acquired immunity. Indeed, although M cells are able to transport lumenal Ags, noninvasive strains of *S. typhimurium* cannot penetrate M cells and are avirulent (Jones et al., *J. Exp. Med.* 180:15-23, 1994). An antigen's immunogenicity and pathogenicity in the GI tract could be the most critical factors in determining whether mucosal immunity or tolerance is induced.

Mucosal tolerance may be the most common immune response because it is necessary to maintain homeostasis. The normal host would readily establish unresponsiveness to commensal bacteria, food Ag and allergens. Taken together, we conclude that our OVA-pσ1 system, M cell targeting of a non-pathogenic protein Ag is an efficient strategy for the establishment of oral tolerance.

Results provided herein clearly show that M cell targeting Ag delivery system reduced the doses of feeding Ag in order to establish oral tolerance. Similar findings were reported using Ag conjugated with B subunit of CT (CT-B) (Sun et al., *Proc. Natl. Acad. Sci.* (*USA*) 91:10795-10799, 1994). That study showed that a single oral administration of relatively small amounts of particulate or soluble antigen coupled to the CT-B markedly suppressed systemic immune responses (Sun et al., *Proc. Natl. Acad. Sci.* (*USA*) 91:10795-10799, 1994). Since CT-B specifically bind to GM-1 ganglioside which abundantly expressed by intestinal epithelial cells (iECs) including M cells, it still remained unclear which of iECs or M cells play a significant role in the induction of oral tolerance. The findings reported herein showed that induction of oral tolerance can be easily achieved by M cell targeting Ag delivery system most likely without Ag uptake from iECs. Recent studies showed that M cells are present in the small intestine of isolated lymphoid follicles (ILFs) as well as intestinal villi (villous M cells) (Hamada et al., *J. Immunol* 168: 57-64, 2002; Jang et al., *Proc. Natl. Acad. Sci.* (*USA*) 101: 6110-6115, 2004). Role(s) of M cells in these newly identified GALT in the induction of oral tolerance are being investigated.

Flow cytometric analysis revealed increased numbers of $CD4^+$ $CD25^+$ T cells in MLNs and spleen of orally tolerized mice, suggesting feeding with OVA-pσ1 induced production of Treg cells. Along this line, a recent study reported that PP-derived Treg clones produce high levels of TGF-β1 and suppressed Ag-specific Ab responses in spleen (Tsuji et al., *Int. Immunol.* 15:525-534, 2003). Based upon these findings, our group examined TGF-pβ1 and IL-10 production by OVA-specific $CD4^+$ T cells from mice fed OVA-pσ1 prior to oral challenge with OVA plus CT. Our results clearly show that $CD4^+$ $CD25^+$ T cells in PPs, MLNs and spleen from orally tolerized mice produce higher levels of TGF-β1 after OVA stimulation than do those from mice fed PBS. On the other hand, intracellular IL-10 production by $CD4^+$ $CD25^+$ T cells from mice fed OVA-pσ1 was significantly reduced. Taken together with the observation that acquired-type $CD4^+$ Treg cells are Ag-specific and produce inhibitory cytokines including TGF-β1 and IL-10 (Cottrez & Groux, *Transplantation* 77:S12-15, 2004), our results indicate that acquired-type $CD4^+$ Treg cells are induced by oral administration of OVA-pσ1.

OVA-specific $CD4^+$ T cells were significantly more reduced in the iLP of orally tolerized mice than in PBS-fed mice challenged with oral OVA plus CT, but no such reduction was seen in spleen or MLNs of either group. Similarly, others showed that a reduction of Ag-specific T cells occurred in mice given repeated low doses of cytochrome c protein (Gutgemann et al., *Immunity* 8:667-673, 1998). In contrast, the spleen of orally tolerized mice exhibited increased numbers of $CD4^+$ $CD25^+$ T cells and the presence of TGF-β1-producing $CD4^+$ $CD25^+$ T cells. Based upon these findings, it appears likely that mechanisms for the induction of mucosal and systemic unresponsiveness differ. Thus, mucosal unresponsiveness is clearly associated with clonal deletion of OVA-specific effector $CD4^+$ T cells while systemic unresponsiveness may be achieved by active suppression of an acquired type of Treg cells. These findings are the first to show that two separate mechanisms underlie mucosal unresponsiveness and that they are entirely distinct from those which underlie systemic unresponsiveness.

It still remains unclear how this clonal deletion of OVA-specific $CD4^+$ T cells actually occurs since $CD4^+$ $CD25^+$ T cells are also reduced significantly in the iLP of orally tolerized mice. However, one can hypothesize that the numbers of OVA-specific $CD4^+$ T cells and AFC in iLP are reduced simply because OVA-specific $CD4^+$ T cell migration into the iLP has been interrupted. Thus, effector $CD4^+$ Th cells could be suppressed by PP-derived TGF-β1-producing $CD25^+$ Treg cells in the MLNs and spleen before reaching the iLP. To support this view, our previous results showed that induction of Ag-specific Ab responses in the iLPs required three consecutive weekly oral immunizations (Kato et al., *J Immunol.* 166:3114-3121, 2001; Fujihashi et al., *J. Exp. Med.* 183: 1929-1935, 1996). We are currently testing this notion using a nasal challenge system in order to better distinguish between OVA-specific $CD4^+$ effector T cell and $CD4^+$ Treg cell activities.

In summary, this example provides the first evidence that M cell targeting of a non-pathogenic Ag OVA-pσ1 can induce mucosal unresponsiveness via a mechanism distinct from that underlying systemic tolerance. This M cell-targeting system allowed us to elucidate the immunoregulatory mechanisms of the PP-mediated oral tolerance pathway from other potential mechanisms. Thus, these findings show that regulatory-type $CD4^+$ T cells are induced in the PP and then migrate into MLNs and spleen. These $CD4^+$ Treg cells contribute to the successful systemic unresponsive state that ensues. Further, these results clearly show that mucosal unresponsiveness to orally administered Ag can be attributed to a lack of Ag-specific $CD4^+$ T helper cells in the iLP.

Nasal Tolerance

From the literature, it has been shown that reovirus type 3 protein sigma 1 (pσ1) is a highly structured protein featuring several domains, which mediate a multi-step interaction between the virus and the host cell (Barton et al., *J. Biol. Chem.* 276:2200-2211, 2000; FIG. 6). It has been shown that type 3 pσ1 interacts with at least two host receptors via separate binding domains. The head domain binds with a component of tight junctions, JAM-1 molecule, whereas sequences contained within the fibrous tail domain binds terminal α-linked sialic acid residues on host cells (Barton et al., *J. Biol. Chem.* 276:2200-2211, 2000; Chappell et al., *J. Virol.* 71:1834, 1997). To determine the relevant binding components of our recombinant pσ1 and OVA-σ1, additional constructs or variants were made and expressed in yeast (FIG. 6).

To determine the role of pσ1's sialic binding domain (SABD), a pσ1(m) construct was made in which the mutations N198→D198 and R202→G202 were introduced to interrupt the SABD's binding activity. In addition, OVA was genetically fused to pσ1(m) and called OVA-pσ1(m). Genetic fusions of OVA are all placed at the N-terminus of pσ1 so as to not interfere with the host receptor binding domains located in the pσ1's C-terminus. Thus, if sialic acid binding dictates mediation of tolerance by pad, then the loss of sialic acid binding should confer immunization. In a similar fashion, the complete removal of pσ1's SABD should do the same, and this variant, OVA-pσ1(Δ), which encompasses the OVA gene fused to the last 207 amino acids of pσ1 renders only a functional trimerizing domain and head (FIG. 6). Each of the OVA fusion proteins featured a flexible linker between the fusion partners.

Siatic Acid Binding is Important For Tolerance Induction by Pσ1

To determine the functional consequence of sialic acid binding by OVA-pσ1, groups of C57BL/6 mice were given three nasal immunizations on days 0, 7, and 14 in combination with the mucosal adjuvant, cholera toxin (CT), and one of three antigens, OVA-σ1, OVA-pσ1(Δ), or OVA or given OVA without CT. Again, OVA-pσ1(Δ) is a truncated OVA-σ1 lacking its SABD and shaft (FIG. 6). To test for a delayed-type hypersensitivity (DTH) reaction, mice were challenged after 42 days with OVA into one ear pinna and PBS into the other ear pinna. Mice immunized with OVA alone or OVA-σ1+CT failed to show swelling in the OVA-challenged ear when compared to mice immunized with OVA+CT ($P<0.001$) or OVA-pσ1(Δ)+CT ($P=0.002$) (FIG. 7). Thus, the OVA-pσ1 (Δ), which lacked the SABD, behaved more as an immunogen in contrast to OVA-pσ1, which behaved as a toleragen. This collective evidence suggested that the presence of the SABD on pσ1 was required for tolerance induction, whereas, in its absence, clearly immunization occurred.

Adoptive Transfer of CD4+ T Cells into Naive Mice Are Unresponsive to OVA Challenge To test whether nasal exposure to OVA-σ1 could make CD4+ T cells unresponsive to OVA and effectively adoptively transfer these T cells, the transgenic DO 11.10 CD4+ T cells were isolated from spleen and lymph nodes by cell-sorting, and adoptively transferred into naive BALB/c mice. After 24 hours, groups of mice were dosed nasally with PBS, 80 µg OVA-σ1, or 400 µg OVA, or given a single i.m. OVA immunization. Three days later, cervical lymph nodes (CLN) were removed and CD4+ T cells were isolated by cell-sorting. These CLN CD4+ T cells (2×10$^6$/mouse) were adoptively transferred into naive mice, and after 24 hrs, they were challenged s.c. with OVA in incomplete Freund's adjuvant. Five days later, CD4+ T cells from the head and neck LN (HNLN) were isolated by cell-sorting and cultured with mitomycin C-treated feeder cells without and with 1.0 mg OVA for 5 days. $^3$H-TdR was used to measure T cell proliferation. Mice were made unresponsive by the nasal 400 µg OVA or the 80 µg OVA-σ1 since these did not proliferate (FIG. 8). In contrast, the CD4+ T cells isolated from the i.m. OVA-dosed mice were responsive. Thus, dosing i.n. with OVA-σ1 can make mice unresponsive to OVA, and this unresponsiveness is mediated by CD4+ T cells specific for OVA. Moreover, this unresponsiveness can be adoptively transferred with CD4+ T cells.

OVA-σ1 Can Be Modified With Encephalitogenic Peptides to Render Protection Against Experimental Autoimmune Encephalitis (EAE) Challenge Thus far, we showed the feasibility of inducing tolerance against OVA, a familiar antigen frequently used in experimental systems. To forward efforts to treating autoimmune diseases, we adapted the OVA-σ1 fusion protein with peptides known to cause autoimmune disease. We hypothesized that genetic fusion of encephalitogenic peptides to OVA-σ1 should induce tolerance as shown with our studies using OVA as a test antigen. OVA-σ1 was modified because we could then follow unresponsiveness to OVA as an internal control for our studies. Thus, this modified OVA-σ1 construct, termed AR1, was made with two copies of the encephalitogenic peptide from proteolipid protein (PLP), PLP$_{139-151}$, separated by an irrelevant peptide (MOG$_{35-55}$) (FIG. 9A). C57BL/6 mice were dosed thrice with AR1, and they did not generate IgG or IgA anti-OVA Abs when compared to OVA+CT-dosed mice (FIG. 9B-D). Subsequent to i.n. challenge with OVA+CT and then tested for a DTH response, no DTH reactions were detected when compared to OVA+CT-dosed mice (FIG. 9E). A separate group of mice also was orally fed AR1 and peripherally challenged with OVA+CT, and these too were unresponsive in this DTH assay. Thus, the modification of OVA-σ1 with encephalitogenic peptides did not interfere with its ability to elicit OVA tolerance.

To test whether tolerance to the fused encephalitogenic peptides was induced by evaluating the efficacy of AR1 against PLP$_{139-151}$ challenge, SJL/J mice were nasally given AR1 as described in FIG. 9. For a positive oral tolerance control group, myelin basic protein was given seven times every 2 days over a 2-wk course. As a negative control group, mice were dosed with PBS. Three wks after the onset of treatments, mice were challenged s.c. with emulsified PLP$_{139-151}$ following standard protocols, and pertussis toxin (PT) was given i.p. A second PT dose was given two days later. Following this challenge protocol, mice typically show clinical disease beginning ~9 days. The AR1 protected against EAE as evidenced by reduced clinical disease (FIG. 10A).

In addition, C57BL/6 mice were nasally dosed with 50 µg myelin oligodendrocyte glycoprotein$_{29-146}$ genetically fused to pσ1 (MOG-pσ1) or to OVA-σ1 (MOG:OVA-pσ1) three times at weekly intervals, and then one week after the last i.n. dose, mice were challenged s.c. with 150 µg MOG$_{35-33}$ on day 0 and 7 of challenge, and given i.v. PT on days 0 and 2. Both the MOG-pσ1 (n=5) and MOG;OVA-σ1 (n=5) protected mice (p<0.001) when compared to PBS-dosed mice (n=5) (FIG. 10B).

Protection against PLP$_{139-151}$ challenge is attributed to the stimulation of the regulatory cytokines, IL-4, IL-10, and TGF-β. SJL mice were dosed with Ar1, OVA-σ1, or PBS as described for FIG. 9. Mice were then challenged with PLP$_{139-151}$ peptide as described for FIG. 10. HNLN, spleens, and MLN were harvested at peak of disease (day 14) and purified CD4+ T cells were restimulated with PLP$_{139-151}$ peptide for two days, and evaluated in a cytokine ELISPOT. PBS- and OVA-pσ1-dosed (unprotected mice) showed elevated (FIG. 11A) IFN-γ and (FIG. 11B) IL-17 cytokine-forming cells (CFC), and no (FIG. 11C) IL-4, (FIG. 11D) IL-10, or (FIG. 11E) TGF-β CFC. In contrast, AR1-dosed (tolerized) mice showed elevated IL-4, IL-10, and TGF-β CFC and no IFN-γ or IL-17 CFC. Thus, only AR1 mice were protected against challenge, and tolerance induced to irrelevant protein (OVA-pσ1) did confer protection.

It was also determined that single nasal or oral dose with MOG-pσ1 protects C57BL/6 mice against challenge with MOG$_{35-55}$. Mice (5/group) were dosed once (FIG. 12A) nasally or (FIG. 12B) orally with 10, 50, or 100 µg of MOG$_{29-146}$-pσ1 (MOG-pσ1) or with PBS, and 10 days later challenged with MOG$_{35-55}$ per description for FIG. 10. In a dose-dependent fashion, protection against autoimmune challenge showed protection, but the 50 µg dose conferred the best protection with no disease, while minimal disease was observed at the 10 or 100 µg doses. Thus, pσ1 delivery in the form of a fusion protein is an effective means to deliver auto-antigens to the mucosa for the development of tolerance to self antigens.

To test whether pσ1-mediated treatment could be therapeutic, a study was performed using MOG-pσ1 to stop further development of EAE. Four groups (5/group) of mice were induced with EAE as described in FIG. 10B. Then, groups were treated with MOG-pσ1 or PBS on day 7 or groups were treated with MOG-pσ1 or PBS on day 10 and 17. Results are shown in FIG. 13. Treatment with MOG-pσ1 demonstrated that protection against further disease development can be conferred suggesting that pσ1-delivered tolerogens can treat autoimmune diseases.

Significance Statement

Studies to date have mostly relied upon oral exposure to induce tolerance (Fujihashi et al., *Acta. Odontol Scand.* 59:301-308, 2001; Mowat, *Nature Rev. Immunol.* 3:331-341, 2003; Weiner, *Microbes & Infection* 3:947-954, 2001) whereas most recently, studies have addressed the potential of adapting i.n. delivery (Collins et al., *Infect. Immun.* 70:2282-2287, 2002; Monfardini et al., *J. Neuroimmunol.* 123:123-134, 2002; Winkler et al., *Clin. Exp. Allergy.* 32:30-36, 2002). The i.n. route clearly has a number of advantages, including less antigen dose required, not subjecting the tolerogen to alteration by the GI tract, and ease of delivery. In addition to considering route of delivery, efficient targeting of tolerogens to mucosal inductive tissues could reduce the amount of material needed for stimulation of tolerance regardless the route of delivery.

A particular strength of the system described herein is that it can be applied to any number of tolerogens that could be successfully fused to pσ1, or another mucosal binding molecule as provided herein. Without meaning to be limited to a single explanation, we propose that pσ1 can circumvent the mucosal barrier and promote the uptake of toleragens by the mucosal immune system, whether mediated via M cells, host epithelial cells, or their combination. Ultimately, T cell responsiveness will occur in the mucosal inductive sites or draining mucosal LN. This toleragen delivery platform has promise in that a single oral administration, and in some instances a single nasal application, can elicit tolerance.

In view of the many possible embodiments to which the principles of the disclosed invention may be applied, it should be recognized that the illustrated embodiments are only preferred examples of the invention and should not be taken as limiting the scope of the invention. We therefore claim as our invention all that comes within the scope and spirit of the description, embodiments of which are described specifically in the following claims.

We claim:

1. A tolerizing fusion protein comprising a targeting portion and an antigen or allergen to which tolerance is desired, wherein the targeting portion comprises a reovirus protein σ1 (pσ1), and wherein administration of the fusion protein to a subject induces tolerance in the subject to the antigen or allergen.

2. The fusion protein of claim 1, wherein the antigen is an autoantigen or therapeutically active biological.

3. A method to induce tolerance in a subject to an antigen or allergen, comprising administering to the subject the fusion protein of claim 1.

4. A method of inducing tolerance in a subject to an antigen, comprising:
administering to the subject a single dose of a tolerizing fusion protein, wherein the tolerizing fusion protein comprises (1) a targeting portion comprising a reovirus protein σ1 (pσ1), and (2) the antigen, thereby inducing tolerance in the subject to the antigen.

5. The method of claim 4, wherein the single dose of the tolerizing fusion protein comprises 1 mg or less of the antigen.

6. The method of claim 5, wherein the single dose of the tolerizing fusion protein comprises 500 μg or less of the antigen.

7. The method of claim 6, wherein the single dose of the tolerizing fusion protein comprises 250 μg or less of the antigen.

8. The method of claim 7, wherein the single dose of the tolerizing fusion protein comprises 100 μg or less of the antigen.

9. A method of inducing antigen specific immune tolerance in a subject, comprising: administering an effective dose of a tolerizing fusion protein comprising a targeting portion and at least one epitope from the antigen to the subject, wherein the tolerizing fusion protein comprises a reovirus protein σ1 (pσ1), thereby inducing tolerance in the subject to the antigen.

10. The method of claim 4, comprising administering more than one tolerizing fusion protein to the subject.

11. The method of claim 4, wherein the tolerizing fusion protein is administered orally or nasally.

12. The method of claim 9, comprising administering more than one tolerizing fusion protein to the subject.

13. The method of claim 9, wherein the tolerizing fusion protein is administered orally or nasally.

14. The method of claim 3, comprising administering more than one fusion protein to the subject.

15. The method of claim 3, wherein the tolerizing fusion protein is administered orally or nasally.

* * * * *

UNITED STATES PATENT AND TRADEMARK OFFICE
CERTIFICATE OF CORRECTION

PATENT NO. : 7,910,113 B2  
APPLICATION NO. : 12/294380  
DATED : March 22, 2011  
INVENTOR(S) : Pascual et al.

Page 1 of 1

It is certified that error appears in the above-identified patent and that said Letters Patent is hereby corrected as shown below:

In the Specification:

In Column 1, line 17, "DE013812" should be --DE138120--

Signed and Sealed this
Fifteenth Day of November, 2011

David J. Kappos
*Director of the United States Patent and Trademark Office*